(12) United States Patent
Sugo

(10) Patent No.: US 11,905,549 B2
(45) Date of Patent: Feb. 20, 2024

(54) METHOD FOR MODIFYING TARGET SITE IN GENOME OF EUKARYOTIC CELL, AND METHOD FOR DETECTING PRESENCE OR ABSENCE OF NUCLEIC ACID SEQUENCE TO BE DETECTED AT TARGET SITE

(71) Applicant: GENAHEAD BIO, INC., Fujisawa (JP)

(72) Inventor: Tsukasa Sugo, Kanagawa (JP)

(73) Assignee: GENAHEAD BIO, INC., Kanagawa (JP)

( * ) Notice: Subject to any disclaimer, the term of this patent is extended or adjusted under 35 U.S.C. 154(b) by 907 days.

(21) Appl. No.: 16/320,699

(22) PCT Filed: Aug. 9, 2017

(86) PCT No.: PCT/JP2017/028898
§ 371 (c)(1),
(2) Date: Jan. 25, 2019

(87) PCT Pub. No.: WO2018/030457
PCT Pub. Date: Feb. 15, 2018

(65) Prior Publication Data
US 2019/0161789 A1    May 30, 2019

(30) Foreign Application Priority Data
Aug. 10, 2016   (JP) ................ 2016-158062

(51) Int. Cl.
| | | |
|---|---|---|
| *C12N 15/09* | (2006.01) | |
| *C12N 15/113* | (2010.01) | |
| *C12N 15/10* | (2006.01) | |
| *C12N 15/87* | (2006.01) | |
| *C12N 9/22* | (2006.01) | |
| *C12Q 1/6806* | (2018.01) | |
| *C12Q 1/68* | (2018.01) | |
| *C12Q 1/686* | (2018.01) | |
| *C12Q 1/6876* | (2018.01) | |

(52) U.S. Cl.
CPC ........... *C12Q 1/6806* (2013.01); *C12N 15/09* (2013.01); *C12N 15/102* (2013.01); *C12N 15/113* (2013.01); *C12N 15/87* (2013.01); *C12Q 1/68* (2013.01); *C12Q 1/686* (2013.01); *C12Q 1/6876* (2013.01); *C12N 9/22* (2013.01); *C12N 2310/20* (2017.05); *C12Q 2543/00* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 8,697,359 | B1 | 4/2014 | Zhang |
| 9,790,490 | B2 * | 10/2017 | Zhang .................... C12N 15/11 |
| 2014/0295557 | A1 | 10/2014 | Joung et al. |
| 2016/0153006 | A1 | 6/2016 | Zhang et al. |
| 2018/0020646 | A1 | 1/2018 | Ueda et al. |

FOREIGN PATENT DOCUMENTS

| | | |
|---|---|---|
| JP | 10-504707 A | 5/1998 |
| JP | 2001-521369 A | 11/2001 |
| JP | 2016-500262 A | 1/2016 |
| JP | 2016-512691 A | 5/2016 |
| JP | 2016-521994 A | 7/2016 |
| WO | WO 95/34202 A1 | 12/1995 |
| WO | WO 97/38087 A2 | 10/1997 |
| WO | WO 2015/131101 A1 | 9/2015 |
| WO | WO 2015/179540 A1 | 11/2015 |
| WO | WO 2016/104716 A1 | 6/2016 |

OTHER PUBLICATIONS

Rong et al., Homologous recombination in human embryonic stem cells using CRISPR/Cas9 nickase and a long DNA donor template. Protein Cell (2014), 5(4):258-260 (Year: 2014).*
Promega (Biomath calculators [online], Promega [retrieved on Nov. 23, 2021], Retrieved from internet https://www.promega.com/resources/tools/biomath (Year: 2021).*
Addgene (https://www.addgene.org/), Addgene #44720 [retrieved on Nov. 23, 2021] (Year: 2021).*
Addgene (https://www.addgene.org/), Addgene #41824 [retrieved on Nov. 23, 2021] (Year: 2021).*
Addgene (https://www.addgene.org/), Addgene #41824 Supp Document, hCRISPR gRNA Synthesis Protocol [retrieved on Nov. 23, 2021] (Year: 2021).*
Addgene vectors #19327 datasheet [retrieved from internet Nov. 30, 2021] https://www.addgene.org/). (Year: 2021).*

(Continued)

*Primary Examiner* — Samuel C Woolwine
*Assistant Examiner* — Catherine Konopka
(74) *Attorney, Agent, or Firm* — Foley & Lardner LLP

(57) ABSTRACT

Provided is a method of modifying a target site in the genome of a eukaryotic cell, the method comprising: (1) a step of introducing into the cell, introduction nucleic acids comprising (a) a template nucleic acid comprising a nucleic acid sequence encoding an RNA-guided nuclease, (b) a template nucleic acid comprising a nucleic acid sequence encoding a guide RNA, or a guide RNA, and (c) a template nucleic acid comprising a nucleic acid sequence encoding a selectable marker; and (2) a step of selecting a cell expressing the selectable marker, wherein the number of moles (C) of (c) the template nucleic acid comprising a nucleic acid sequence encoding a selectable marker, subjected to the step (1), is smaller than any of the number of moles (A) of (a) the template nucleic acid comprising a nucleic acid sequence encoding an RNA-guided nuclease and the number of moles (B) of (b) the template nucleic acid comprising a nucleic acid sequence encoding a guide RNA, or the guide RNA.

4 Claims, 16 Drawing Sheets

Specification includes a Sequence Listing.

(56) References Cited

OTHER PUBLICATIONS

Addgene vectors #19329 datasheet, [retrieved from internet Nov. 30, 2021] https://www.addgene.org/). (Year: 2021).*
Addgene vectors #11349 datasheet, [retrieved from internet Nov. 30, 2021] https://www.addgene.org/). (Year: 2013).*
Addgene vectors #42230 datasheet, [retrieved from internet Nov. 30, 2021] https://www.addgene.org/). (Year: 2021).*
Shy et al., Co-incident insertion enables high efficiency genome engineering in mouse embryonic stem cells. Nucleic Acids Research (published Aug. 2, 2016) 44:16, 7997-8010. (Year: 2016).*
Dickinson et al., Engineering the Caenorhabditis elegans genome using Cas9-triggered homologous recombination. Nat Methods (2013) 10:10, 1028-1034 and Supplemental materials (Year: 2013).*
Zhang et al., Off-target Effects in CRISPR/Cas9-mediated Genome Engineering. Molecular Therapy—Nucleic Acids (2015) 4, e264 (Year: 2015).*
Pinder et al., Nuclear domain 'knock-in' screen for the evaluation and identification of small molecule enhancers of CRISPR-based genome editing. Nucleic Acids Research (2015), 43(19): 9379-9392 (Year: 2015).*
Addgene vectors #122508, #45457 and #42230 datasheets, [retrieved from internet Apr. 20, 2022] https://www.addgene.org (Year: 2022).*
Biomath calculators [online], Promega [retrieved on Apr. 20, 2021], https://www.promega.com/resources/tools/biomath/ (Year: 2022).*
Lawhorn et al., Evaluation of sgRNA Target Sites for CRISPR-Mediated Repression of TP53. PLOS One (2014), 9(11), e113232, pp. 1-8 (Year: 2014).*
Berman et al., "Ultra-Sensitive Quantification of Genome Editing Events Using Droplet Digital PCR," Bio-Rad Laboratories, Inc., Jan. 2015, Bulletin 6712, Rev. A, 6 pages, retrieved from URL https://www.salk.edu.wp-content/uploads/2017/11/CRISPR_technote.pdf on May 6, 2020.
Supplementary European Search Report dated May 14, 2020 in EP 17839525.7.
Whale et al., "Fundamentals of multiplexing with digital PCR," Biomolecular Detection and Quantification, May 27, 2016, 10:15-23.
Office Action dated Mar. 31, 2020, in JP 2018-533531.
Supplementary Partial European Search Report dated Mar. 9, 2020, in EP 17839525.7.
Pinder et al., "Nuclear domain 'knock-in' screen for the evaluation and identification of small molecule enhancers of CRISPR-based genome editing," Nucleic Acids Research, Oct. 1, 2015, 43(19):9379-9392.
Russell et al., "Engineering herpes simplex viruses by infection-transfection methods including recombination site targeting by CRISPR/Cas9 nucleases," Journal of Virological Methods, 2015 (Dec. 3, 2014), 213:18-25.
International Search Report dated Nov. 7, 2017, in PCT/JP2017/028898.
Miyaoka et al., "Systematic quantification of HDR and NHEJ reveals effects of locus, nuclease, and cell type on genome-editing," Scientific Reports, Mar. 31, 2016, 6:23549, 1-12.
Thermo Fisher Scientific Learning at the Bench, Nov. 27, 2015, 3 pages.
Zetsche et al., "Cpf1 is a Single RNA-Guided Endonuclease of a Class 2 CRISPR-Cas System," Cell, Oct. 22, 2015, 163:759-771.

* cited by examiner

FIG. 5

```
         10        20        30        40        50        60
tctattttatttagAGCTTAACTTAGATAGCAGTAATTTCCCTGGAGTAAAACTGCGGTC
               L  N  L  D  S  S  N  F  P  G  V  K  L  R  S
    gRNA RECOGNITION SEQUENCE
    -------------------------->

70        80        90       100       110       120
AAAAATGTCCCTCCGTTCTTATGGAAGCCGGGAAGGATCTGTATCAAGCCGTTCTGGAGA
 K  M  S  L  R  S  Y  G  S  R  E  G  S  V  S  S  R  S  G  E 130       140       150       160       170       180
GTGCAGTCCTGTTCCTATGGGTTCATTTCCAAGAAGAGGGTTTGTAAATGGAAGCAGAGA
 C  S  P  V  P  M  G  S  F  P  R  R  G  F  V  N  G  S  R  E 190       200       210       220       230       240
AAGTACTGGATATTTAGAAGAACTTGAGAAAGAGGgtaactttcttcatatagtaaac
 S  T  G  Y  L  E  E  L  E  K  E  R
```

FIG. 6

AMPLIFICATION PRODUCT FROM WILD-TYPE APC GENE 1256bps

CTTGCACAGAGACTCCCCATAATCACCATTATCTCAAAATATCACTATTATTATTTGGCCATGATTTATTTATTAATAATGAATAATAGGTAATATATATAAGGTGCGTGCTTTGAGAGTGATCTGAATTTTTTC
TCAGCATACTTAAATGTCAAGAAATACAGAATCATGTCTTGAAGTTATTTAGAATTTCATGTTAATATATTGTGTTCTTTTTAACAGGAAGTACTTAAACAACTACAAGGAAGTATTGAAGATGAAGCTATGGC
TTCTTCTGGACAGATTGATTTATTAGAGCGTCTTAAAGGTAGATTTTAAAAAGGTGTTTTAAAATAATTTTTTAAGCTCAAATTGTCATCTTTAGGTGTGTAGATCCAAGTACAGCTTCTCTCGATTTGGGTGTT
GGTATCAGTTTTCTTGGTATGTTAGCCTTACCCTCAGGATGTAATTGTTAAAGTACAAATAAATAAAAAATGTATTTGTGTGTCATTTCTTCAGTTAAACATTTAACTGGCTTTGAATGAACTATTTTAAATCCCT
CCCTTAAATAATTTTCGGCTCTTTGTAAAGCTTGTTGCTATTCTGCCAGTCACTAAATAGGGCTTAGTATTCTATATGCCATAGACTTGAGCCTACTGTTTCATTGGAAGAAGTATTGTCTTCTTCATTCAGGAT
AGAAATACTTTAACCTTTTCACATATATAAGTTGATTATAATTCATTTTTAGCAGTTTTAAAAGGGATATCTTTCTCATTCTGTTGCTTGAAAATTCCAGTGTCAGAACAGAGAAAGTGCTTGATAATAATTGAAGC
CAGACAGAGAAATTACTTTTGGATTCTAAAATATTATTTAGAGGAAGTCTAAGGAAGTACATTTTATCTAATTTCCTTTAACACACTCCTTATTTTTACCCTGACCCAAGTGGACTTTTCAGGGAAAGTCCTAA
ATAATTTTTGTTTTCAGTCATGTATATTTGTGGTTAAAATGTAAACCTAATATTTCACTTTAAAATAATATAACATTAAGAATATTTTAGACTGCTTAAAGCAATTGTTGTATAAAAACTTGTTTCTATTTATTTA
GAGCTTAACTTAGATAGCAGTAATTTCCCTGGAGTAAAACTGCGGTCAAAAATGTCCCATGGGTTCATTTCCAAGAAGAGGGTTTGTAAATGGAAGCAGAGAAAGT
TTCCAAGAAGAGGGTTTGTAAATGGAAGCAGAGAAAGT

AMPLIFICATION PRODUCT OF APC GENE INTO WHICH ARTIFICIAL NUCLEIC ACID IS INSERTED 1191bps CTTGCACAGAGACTCCCCATAATCACCATTATCTCAAAATATCACTATTATTATTTGGCCATGATTTATTTATTAATAATGAATAATAGGTAATATATAT
AAGGTGCGTGCTTTGAGAGTGATCTGAATTTTTTCTCAGCATACTTAAATGTCAAGAAATACAGAATCATGTCTTGAAGTTATTTAGAATTTCATGTT
AATATATTGTGTTCTTTTTAACAGGAAGTACTTAAACAACTACAAGGAAGTATTGAAGATGAAGCTATGGCTTCTTCTGGACAGATTGATTTATTAGA
GCGTCTTAAAGGTAGATTTTAAAAAGGTGTTTTAAAATAATTTTTTAAGCTCAAATTGTCATCTTTAGGTGTGTAGATCCAAGTACAGCTTCTCTCGAT
TTGGGTGTTGGTATCAGTTTTCTTGGTATGTTAGCCTTACCCTCAGGATGTAATTGTTAAAGTACAAATAAATAAAAAATGTATTTGTGTGTCATTTCT
TCAGTTAAACATTTAACTGGCTTTGAATGAACTATTTTAAATCCCTCCCTTAAATAATTTTCGGCTCTTTGTAAAGCTTGTTGCTATTCTGCCAGTCACT
AAATAGGGCTTAGTATTCTATATGCCATAGACTTGAGCCTACTGTTTCATTGGAAGAAGTATTGTCTTCTTCATTCAGGATAGAAATACTTTAACCTT
TTCACATATATAAGTTGATTATAATTCATTTTTAGCAGTTTTAAAAGGGATATCTTTCTCATTCTGTTGCTTGAAAATTCCAGTGTCAGAACAGAGAAAG
TGCTTGATAATAATTGAAGCCAGACAGAGAAATTACTTTTGGATTCTAAAATATTATTTAGAGGAAGTCTAAGGAAGTACATTTTATCTAATTTTCCTT
TAACACACTCCTTATTTTTACCCTGACCCAAGTGGACTTTTCAGGGAAAGTCCTAAATAATTTTTGTTTTCAGTCATGTATATTTGTGGTTAAAATGTAA
ACCTAATATTTCACTTTAAAATAATATAACATTAAGAATATTTTAGACTGCTTAAAGCAATTGTTGTATAAAAACTTGTTTCTATTTATTTAGAGCTTA
ACTTAGATAGCAGTAATTTCCCTGGAGTAAAACTGCGGTCAAAAATGTCCCATGGGTTCATTTCCAAGAAGAGGGTTTGTAAATGGAAGCAGAGAA
AGT

FIG. 14

```
         10        20        30        40        50        60
TCTGCTGCCTGTCTGAAAATGGGGATTGGAATTGCAGGCACCCAACTGTCCGGCCTGAGC
 S  A  A  C  L  K  M  G  I  G  I  A  G  T  Q  L  S  G  L  S
         70        80        90       100       110       120
GAGCCTCCCCACCTGGTCACCCAGGCCCCGGGCCGCAGTGGGGAGGGCGAGGCCCGGGCT
 E  P  P  H  L  V  T  Q  A  P  G  R  S  G  E  G  E  A  R  A
        130       140       150       160       170       180
TCAGCTCACCCTTCACCCCATGTTCTCCTCAGGTCATTGGCAGCTCCTCCTCTTCATC
 S  A  H  P  S  P  P  C  S  P  Q  V  I  G  S  S  L  L  F  I
        190       200       210       220       230       240
CACGACAAGAAGGAACAGGCCAAAGTGTGGATGATCGACTTTGGGAAAACCACGCCCCTG
 H  D  K  K  E  Q  A  K  V  W  M  I  D  F  G  K  T  T  P  L
        250       260       270       280       290       300
CCTGAGGGCCAGACCCTGCAGCATGACGTCCCCTGGCAGGAGGGGAACCGGGAGGATGGC
 P  E  G  Q  T  L  Q  H  D  V  P  W  Q  E  G  N  R  E  D  G
        310       320       330       340       350       360
TACCTCTCGGGGCTCAATAACCTCGTCGACATCCTGACCGAGATGTCCCAGGATGCCCCA
 Y  L  S  G  L  N  N  L  V  D  I  L  T  E  M  S  Q  D  A  P
?
CTCGCCTGAGCTGCCCACGCCCTCCCTGGCCCCGCCTGGGCCTCCTTTCCTCCTCCTGT
 L  A  *
```

METHOD FOR MODIFYING TARGET SITE IN GENOME OF EUKARYOTIC CELL, AND METHOD FOR DETECTING PRESENCE OR ABSENCE OF NUCLEIC ACID SEQUENCE TO BE DETECTED AT TARGET SITE

CROSS-REFERENCE TO RELATED APPLICATIONS

This application is the U.S. National Stage of PCT/JP2017/028898, filed Aug. 9, 2017, which claims priority to JP 2016-158062, filed Aug. 10, 2016.

SEQUENCE LISTING

The instant application contains a Sequence Listing which has been submitted electronically in ASCII format and is hereby incorporated by reference in its entirety. Said ASCII copy, created on Mar. 8, 2022, is named 120543-0102_SL.txt and is 12,549 bytes in size.

TECHNICAL FIELD

The present invention relates to a method of modifying a target site in the genome of a eukaryotic cell. In particular, the present invention relates to a method of modifying, via genome editing, a target site in the genome of a eukaryotic cell in vitro or ex vivo.

BACKGROUND ART

In genome editing (see Patent Literature 1), DNA double-strand break (DSB) is introduced into a particular site in genome with a site-specific nuclease, and a gene of interest is inserted (knock-in) into the site cleaved by the nuclease via a DSB repair mechanism with homologous recombination (HR).

For the knock-in through HR, when a modification to be performed is for about several to tens of bases, such as introduction of a single nucleotide polymorphism (SNP) and insertion of a short tag sequence, a method can be adopted involving inserting a single-strand oligodeoxynucleotide (ssODN) into the site cleaved by the nuclease.

On the other hand, for the knock-in through HR, when a modification to be performed is for more than several to tens of bases, a targeting vector (also referred to as a "donor vector"), which carries a gene to be inserted, is used. The targeting vector has a structure in which a targeting cassette, which includes the gene to be inserted, is flanked by two homology arms for causing HR. Knock-in through DSB and HR can be achieved by transfection of cells with the targeting vector along with an expression vector incorporating an RNA-guided nuclease (for example, a Cas9 nuclease or a Cas9 nickase, or variants thereof) and an expression vector incorporating a guide RNA (gRNA).

Examples of factors that affect the efficiency of knock-in through HR include an "off-target effect" and a "random integration." The off-target effect refers to effects caused by introduction of DSB into a site other than the target site in the genome by the nuclease. When the off-target effect occurs, an error caused by repair of DSB with non-homologous end-joining (NHEJ) may bring about an unexpected gene disruption. The random integration refers to that the incorporation of targeting vector cassette into the genome rather than through DSB and HR in a random manner. The random integration may also bring about an unexpected gene disruption.

In relation to the off-target effect, Patent Literature 2 discloses a method of increasing specificity of the genome editing using a truncated guide RNA (tru-gRNA). The gRNA comprises a complementary region that binds to a DNA sequence of the target site through base-pairing and an RNA-guided nuclease binding region, and this method uses, as the gRNA, a tru-gRNA having a truncated target complementary region (less than 20 nts).

In order to confirm insertion of an exogenous nucleic acid sequence into the genome via HR, a method has conventionally been used involving performing PCR on the genome as a template using a primer designed for the outside (upstream or downstream) of the homology arms and a primer designed for the inside of the exogenous nucleic acid sequence. This method is an approach to confirmation of the insertion of the exogenous nucleic acid sequence into the genome by detecting amplification products having a base length of interest. It was not possible for this method to evaluate the efficiency of inserting the exogenous nucleic acid sequence into the genome via HR (knock-in efficiency) because the detection of amplification products in PCR lacks quantitativeness. Moreover, even if a random integration occurs, it was not possible for this method to detect that.

CITATION LIST

Patent Literature

Patent Literature 1: National Publication of International Patent Application No. 2016-500262
Patent Literature 2: National Publication of International Patent Application No. 2016-512691

SUMMARY OF INVENTION

Technical Problem

The main object of the present invention is to provide a technology for modifying a target site in the genome of a cell with a high specificity and efficiency, using a template nucleic acid of an RNA-guided nuclease and a template nucleic acid of a gRNA, or a gRNA. From another point of view, the problem for the present invention is to efficiently select cells in which a desired modification is produced at the target site in the genome.

Solution to Problem

In order to solve the problem described above, the present invention provides the following [1] to [8].
[1] A method of modifying a target site in the genome of a eukaryotic cell, the method comprising:
(1) a step of introducing into the cell, introduction nucleic acids comprising
  (a) a template nucleic acid comprising a nucleic acid sequence encoding an RNA-guided nuclease,
  (b) a template nucleic acid comprising a nucleic acid sequence encoding a guide RNA, or a guide RNA, and
  (c) a template nucleic acid comprising a nucleic acid sequence encoding a selectable marker; and
(2) a step of selecting a cell expressing the selectable marker, wherein
the number of moles (C) of (c) the template nucleic acid comprising a nucleic acid sequence encoding a selectable marker, subjected to the step (1), is smaller than any of the number of moles (A) of (a) the template nucleic acid comprising a nucleic acid sequence encoding an RNA-guided nuclease and the number of moles (B) of (b) the template nucleic acid comprising a nucleic acid sequence encoding a guide RNA, or the guide RNA (in this description, may be referred to as the "method of the present invention").

[2] The method according to [1], wherein the introduction nucleic acids in the step (1) comprise (d) a targeting template nucleic acid comprising an exogenous nucleic acid sequence, and the number of moles (C) of (c) the template nucleic acid comprising a nucleic acid sequence encoding a selectable marker, subjected to the step (1), is smaller than any of the number of moles (A) of (a) the template nucleic acid comprising a nucleic acid sequence encoding an RNA-guided nuclease, the number of moles (B) of (b) the template nucleic acid comprising a nucleic acid sequence encoding a guide RNA, or the guide RNA, and the number of moles (D) of (d) the targeting template nucleic acid comprising an exogenous nucleic acid sequence.

[3] The method according to [1] or [2], wherein the ratio of the number obtained by multiplying the number of moles (C) of (c) the template nucleic acid comprising a nucleic acid sequence encoding a selectable marker by the number of types (n) of the introduction nucleic acids to the total number of moles of the introduction nucleic acids subjected to the step (1) (C×n/(the total number of moles of the introduction nucleic acids)) is 0.01 to 0.8.

[4] The method according to [1], wherein the introduction nucleic acids subjected to the step (1) consist of (a) the template nucleic acid comprising a nucleic acid sequence encoding an RNA-guided nuclease, (b) the template nucleic acid comprising a nucleic acid sequence encoding a guide RNA, or the guide RNA, and (c) the template nucleic acid comprising a nucleic acid sequence encoding a selectable marker, and wherein the ratio of the number obtained by multiplying the number of moles (C) of (c) the template nucleic acid comprising a nucleic acid sequence encoding a selectable marker by the number of types (3) of the introduction nucleic acids to the total of the number of moles (A) of (a) the template nucleic acid comprising a nucleic acid sequence encoding an RNA-guided nuclease, the number of moles (B) of (b) the template nucleic acid comprising a nucleic acid sequence encoding a guide RNA, or the guide RNA, and the number of moles (C) of (c) the template nucleic acid comprising a nucleic acid sequence encoding a selectable marker (C×3/(A+B+C)) is 0.01 to 0.8.

[5] The method according to [2], wherein the introduction nucleic acids subjected to the step (1) consist of (a) the template nucleic acid comprising a nucleic acid sequence encoding an RNA-guided nuclease, (b) the template nucleic acid comprising a nucleic acid sequence encoding a guide RNA, or the guide RNA, (c) the template nucleic acid comprising a nucleic acid sequence encoding a selectable marker, and (d) the targeting template nucleic acid comprising an exogenous nucleic acid sequence, and wherein the ratio of the number obtained by multiplying the number of moles (C) of (c) the template nucleic acid comprising a nucleic acid sequence encoding a selectable marker by the number of types (4) of the introduction nucleic acids to the total of the number of moles (A) of (a) the template nucleic acid comprising a nucleic acid sequence encoding an RNA-guided nuclease, the number of moles (B) of (b) the template nucleic acid comprising a nucleic acid sequence encoding a guide RNA, or the guide RNA, the number of moles (C) of (c) the template nucleic acid comprising a nucleic acid sequence encoding a selectable marker, and the number of moles (D) of (d) the targeting template nucleic acid comprising an exogenous nucleic acid sequence (C×4/(A+B+C+D)) is 0.01 to 0.8.

[6] The method according to any of [1] to [5], wherein any of the introduction nucleic acids is a plasmid vector.

[7] The method according to any of [1] to [6], wherein the selectable marker is a drug resistance gene.

[8] The method according to any of [1] to [7], wherein the RNA-guided nuclease is a Cas9 nuclease or a Cas9 nickase.

[9] The method according to any of [1] to [7], wherein the RNA-guided nuclease is a Cpf1 nuclease.

[9a] A method of evaluating an efficiency of inserting the exogenous nucleic acid sequence into the genome in the cell subjected to the method according to any of [1] to [9], comprising (A) a step of performing digital PCR on the genome of the cell as a template using a probe designed for the outside of homology arms and a probe designed for the inside of a targeting cassette.

[10] A method for detecting the presence or absence of a nucleic acid sequence to be detected at a predetermined locus on a chromosome, the method comprising:

(2) a step of detecting, via a digital PCR method, the presence or absence of hybridization, to a genomic DNA fragment derived from the chromosome, of a first probe nucleic acid that hybridizes to all or part of the nucleic acid sequence to be detected, and a second probe nucleic acid that hybridizes to a nucleic acid sequence other than the nucleic acid sequence to be detected in the predetermined locus; and (3) a step of detecting the presence of the nucleic acid sequence to be detected at the predetermined locus when the first probe nucleic acid and the second probe nucleic acid are hybridized to the genomic DNA fragment and double-positive is detected, and of detecting the absence of the nucleic acid sequence to be detected at the predetermined locus when double-positive is not detected.

[11] The method according to [10], wherein a first region to which the first probe nucleic acid can hybridize and a second region to which the second probe nucleic acid hybridizes are separated by a predetermined base length.

[12] The method according to [11], comprising, prior to the step (2), (1) a step of preparing the genomic DNA fragment from a test cell.

[13] The method according to [12], wherein the nucleic acid sequence to be detected is an exogenous nucleic acid sequence contemplated to be inserted into, via genetic recombination, a locus of interest on a chromosome of the test cell, and wherein the first probe nucleic acid hybridizes to all or part of the exogenous nucleic acid sequence, and the second probe nucleic acid hybridizes to a nucleic acid sequence in the locus of interest that is not located between two homology arms subjected to the genetic recombination.

[13a] The method according to [13], wherein the presence of the exogenous nucleic acid sequence is detected at a locus other than the locus of interest based on the fact that the double-positive is not obtained and that hybridization of the first probe nucleic acid to the genomic DNA fragment is detected.

[13b] The method according to [13], wherein the absence of the exogenous nucleic acid sequence is detected on the chromosome based on the fact that the double-positive is not obtained and that hybridization of the second probe nucleic acid to the genomic DNA fragment is detected.

[13c] The method according to any of [14] to [17], wherein:
in the step (1), a genomic DNA fragment is prepared from a cell population of the test cell;
in the step (2), hybridization of the first probe nucleic acid and the second probe nucleic acid to the genomic DNA fragment is quantified; and
in the step (3), any one or more of the following ratios in the cell population is calculated from a hybridization amount (DP) of the first probe nucleic acid and the second probe nucleic acid, a hybridization amount (SP1) of the first probe nucleic acid alone, and/or a hybridization amount (SP2) of the second probe nucleic acid alone.

Insertion percentage of exogenous nucleic acid sequence into locus of interest (%)=$DP \times 100/(DP+SP2)$ Random integration percentage of exogenous nucleic acid sequence into chromosome (%)=$SP1 \times 100/(DP+SP2)$

[13d] The method according to [13c], further comprising:
(4) a step of using a probe pair that hybridizes to the chromosome with the distance of a base length corresponding to the base length between the first region and the second region and quantifying hybridization of the probe pair to the genomic DNA fragment via a digital PCR method,
such that the following ratio in the genomic DNA fragment is calculated from a hybridization amount (dp) of both probes of the probe pair and a hybridization amount (sp) of either one of the probe pair:

Fragmentation percentage (%)=$<sp> \times 100/(dp+<sp>)$ (wherein, $<sp>$ denotes an average value of hybridization amounts of each probe of the probe pair); and
(5) a step of correcting the insertion percentage (%) with the fragmentation percentage (%).

[13e] The method according to any of [13a] to [13d], wherein the first region to which the first probe nucleic acid can hybridize and the second region to which the second probe nucleic acid hybridizes are separated by at least 1 kb length in the locus of interest.

[14] The method according to [12], wherein the nucleic acid sequence to be detected is an endogenous nucleic acid sequence contemplated to be deleted from, via genetic recombination, a locus of interest on a chromosome of the test cell, and
wherein the first probe nucleic acid hybridizes to all or part of the endogenous nucleic acid sequence, and
the second probe nucleic acid hybridizes to a nucleic acid sequence in the locus of interest that is not located between two homology arms subjected to the genetic recombination.

[14a] The method according to [14], wherein the absence of the endogenous nucleic acid sequence is detected at the locus of interest based on the fact that the double-positive is not obtained and that hybridization of the second probe nucleic acid to the genomic DNA fragment is detected.

[14b] The method according to [14], wherein the presence of the endogenous nucleic acid sequence is detected at the locus of interest based on the fact that the first probe nucleic acid and the second probe nucleic acid are hybridized to the genomic DNA fragment and double-positive is detected.

[14c] The method according to [14a] or [14b], wherein:
in the step (1), a genomic DNA fragment is prepared from a cell population of the test cell;
in the step (2), hybridization of the first probe nucleic acid and the second probe nucleic acid to the genomic DNA fragment is quantified; and
in the step (3), the following ratio in the cell population is calculated from a hybridization amount (DP) of the first probe nucleic acid and the second probe nucleic acid, and a hybridization amount (SP2) of the second probe nucleic acid alone.

Deletion percentage of endogenous nucleic acid sequence (%)=$100-DP \times 100/(DP+SP2)$

[14d] The method according to [14c], further comprising:
(4) a step of using a probe pair that hybridizes to the chromosome with the distance of a base length corresponding to the base length between the first region and the second region and quantifying hybridization of the probe pair to the genomic DNA fragment via a digital PCR method,
such that the following ratio in the genomic DNA fragment is calculated from a hybridization amount (dp) of both probes of the probe pair and a hybridization amount (sp) of either one of the probe pair:

Fragmentation percentage (%)=$<sp> \times 100/(dp+<sp>)$ (wherein, $<sp>$ denotes an average value of hybridization amounts of each probe of the probe pair); and
(5) a step of correcting the deletion percentage (%) with the fragmentation percentage (%).

[14e] The method according to any of [14a] to [14d], wherein the first region to which the first probe nucleic acid can hybridize and the second region to which the second probe nucleic acid hybridizes are separated by at least 1 kb length in the locus of interest.

[15] The method according to any of [10] to [12], wherein the presence of the nucleic acid sequence to be detected is detected at a locus other than the predetermined locus based on the fact that the double-positive is not obtained and that hybridization of the first probe nucleic acid to the genomic DNA fragment is detected.

[16] The method according to any of [10] to [12], wherein the absence of the nucleic acid sequence to be detected is detected on the chromosome based on the fact that the double-positive is not obtained and that hybridization of the second probe nucleic acid to the genomic DNA fragment is detected.

Advantageous Effects of Invention

According to the present invention, a technology for modifying a target site in the genome of a cell with a high specificity and efficiency, using a template nucleic acid of an RNA-guided nuclease and a template nucleic acid of a gRNA, or a gRNA is provided. In addition, a technology for efficiently selecting cells in which a desired modification is produced at the target site in the genome is provided.

BRIEF DESCRIPTION OF DRAWINGS

FIG. 5 shows a nucleotide sequence of exon 3 of APC gene and a gRNA recognition sequence (Example 1). FIG. 5 discloses SEQ ID NOS 27-28, respectively, in order of appearance.

FIG. 6 shows nucleotide sequences of an amplification product of wild-type APC gene and of an amplification product of APC gene into which an artificial nucleic acid (exogenous nucleic acid sequence) is inserted (Example 1). FIG. 6 discloses SEQ ID NOS 5-6, respectively, in order of appearance.

FIG. 14 shows a nucleotide sequence of exon 8 of IPTKB gene and a gRNA recognition sequence (Example 4). FIG. 14 discloses SEQ ID NOS 25-26, respectively, in order of appearance.

DESCRIPTION OF EMBODIMENTS

Figure 1:
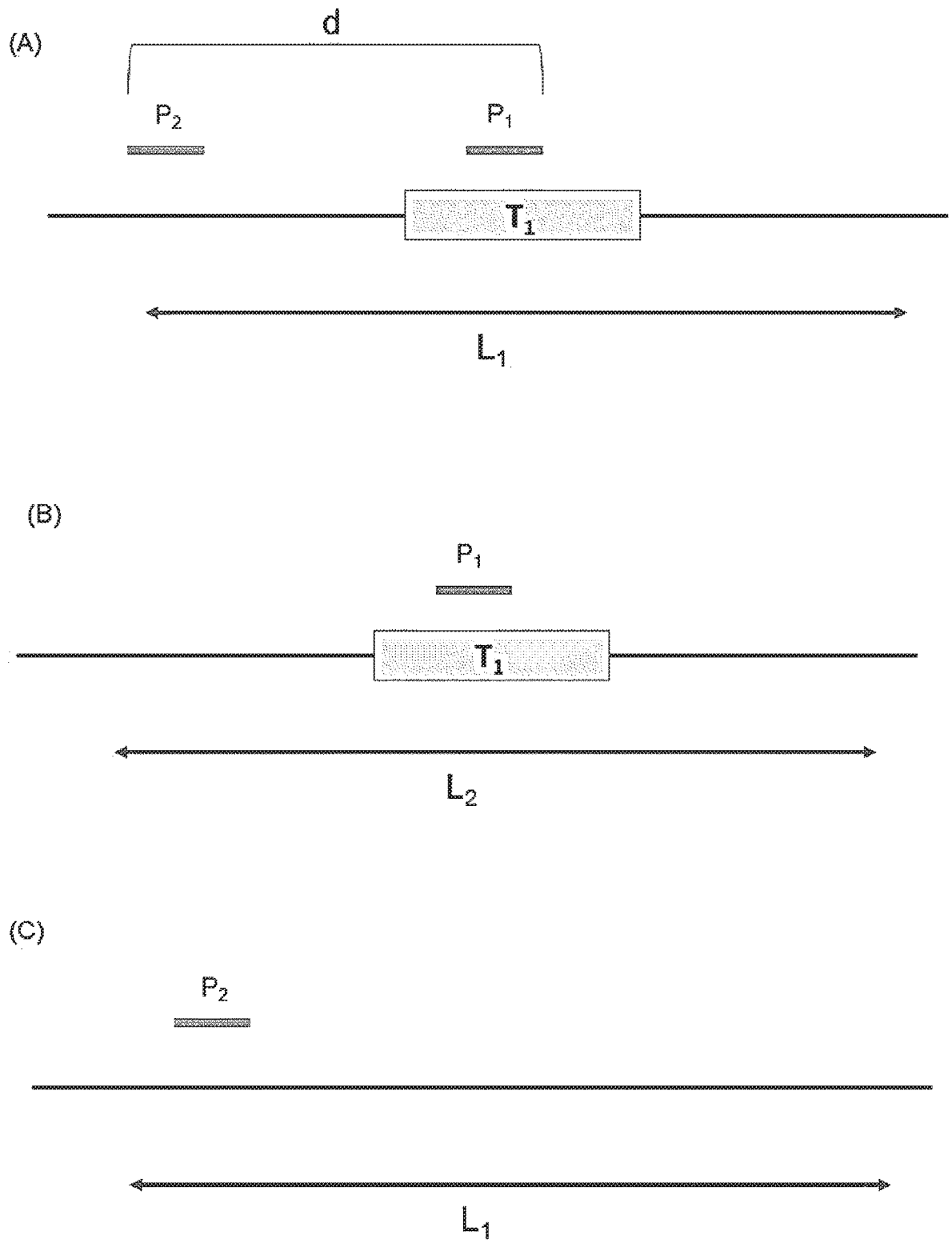
FIG. 1 describes a method of detecting the presence or absence of a nucleic acid sequence to be detected at a predetermined locus on a chromosome, according to the present invention.

Hereinafter, suitable embodiments for carrying out the present invention will be described with reference to the drawings. Note that the embodiments described below only illustrate one example of representative embodiments of the present invention, and the scope of the present invention should not be narrowly construed by this.

1. Method of Modifying Target Site in Genome

Examples of methods of modifying a target site in the genome, according to the present invention, include a modification method through a genetic recombination method known per se (such as non-homologous end-joining (NHEJ)) (knockout and knock-in methods), a modification method through homologous recombination (HR) (knock-in method), a modification method through homology-directed repair (HDR) (knock-in method), and a modification method through microhomology-mediated end joining (MMEJ) (knock-in method). Examples of knockout methods according to the present invention include those in which a gene is modified through an insertion and/or deletion (InDel) mutation that occurs when DSB caused by an RNA-guided nuclease is repaired. On the other hand, examples of knock-in methods according to the present invention include those in which a gene is modified through insertion of an appropriate exogenous nucleic acid sequence into a DNA double-strand break (DSB) site caused by an RNA-guided nuclease.

A certain embodiment of the present invention is a method of modifying a target site in the genome of a eukaryotic cell, the method comprising the following steps:

(1) a step (hereinafter, also referred to as a "transfection step (1)") of introducing into the cell, introduction nucleic acids comprising (a) a template nucleic acid comprising a nucleic acid sequence encoding an RNA-guided nuclease (hereinafter, also referred to as a "nuclease template nucleic acid"), (b) a template nucleic acid comprising a nucleic acid sequence encoding a guide RNA (hereinafter, also referred to as a "gRNA template nucleic acid"), or a guide RNA, and (c) a template nucleic acid comprising a nucleic acid sequence encoding a selectable marker (hereinafter, also referred to as a "selection template nucleic acid"); and (2) a step (hereinafter, also referred to as a "selection step (2)") of selecting a cell expressing the selectable marker.

In a certain embodiment of the present invention, a gene at a target site can be knocked out via NHEJ using a nuclease template nucleic acid, and a gRNA template nucleic acid or a gRNA. In the knockout via NHEJ using a nuclease template nucleic acid, and a gRNA template nucleic acid or a gRNA, it is preferable that a sufficient amount of the RNA-guided nuclease and the gRNA be expressed in the cell.

By allowing a sufficient amount of the RNA-guided nuclease and the gRNA to be expressed in the cell, DSB is brought about at a frequency sufficient for knockout and the gene at the target site can be knocked out with a high efficiency.

In knockout methods according to the present invention, cells in which the desired genome target site has been knocked out can be obtained with a high efficiency by subjecting a smaller number of moles of the selection template nucleic acid, compared to any of the nuclease template nucleic acid, and the gRNA template nucleic acid or the gRNA, to the transfection step (1), and by only selecting the cell expressing the selectable marker in the selection step (2).

Examples of cells selected in the selection step (2) include a cell that has been able to express a sufficient amount of selectable markers even when a small amount of the selection vector was subjected to the transfection step (1). That is, the cells selected in the selection step (2) are those with a high uptake efficiency of the selection template nucleic acid, or those with a high expression efficiency of the selection template nucleic acid taken up. From this, in these cells, any of the uptake efficiency and the expression efficiency of the nuclease template nucleic acid, and the gRNA template nucleic acid or the gRNA is high, and as a result, DSB is brought about at a high frequency and the gene at the target site can be knocked out through NHEJ with a high probability.

In knockout methods according to the present invention, a high knockout efficiency cells can be obtained by subjecting a smaller number of moles of the selection template nucleic acid, compared to any of the nuclease template nucleic acid, and the gRNA template nucleic acid or the gRNA, to the transfection step (1), and by only selecting the cell expressing the selectable marker in the selection step (2).

Another embodiment of the present invention is a method of inserting an exogenous nucleic acid sequence into a target site in the genome of a eukaryotic cell, wherein the introduction nucleic acids in the transfection step (1) comprise (d) a targeting template nucleic acid comprising an exogenous nucleic acid sequence (hereinafter, also simply referred to as a "targeting template nucleic acid").

In the knock-in via HR using a nuclease template nucleic acid, a gRNA template nucleic acid or a gRNA, and a targeting template nucleic acid, in the first place, it is preferable that a sufficient amount of the RNA-guided nuclease and the gRNA be expressed in the cell, and furthermore, it is preferable that an appropriate amount of the targeting template nucleic acid be introduced into the cell.

When a sufficient amount of the RNA-guided nuclease and the gRNA is not expressed in the cell, factors necessary for the knock-in via HR are not complete, and the frequency of random integrations that are not caused by DSB and HR may be increased.

Even when a sufficient amount of the RNA-guided nuclease and the gRNA is expressed in the cell, if the amount of the targeting template nucleic acid introduced is too little compared to the amount of the RNA-guided nuclease and the gRNA expressed, then DSB may be repaired predominantly through NHEJ rather than HR, leading to a remarkable gene disruption, which is not aimed at. On the other hand, when the amount of the targeting template nucleic acid introduced is excessive compared to the amount of the RNA-guided nuclease and the gRNA expressed, then the frequency of random integrations that are not caused by DSB and HR may be increased. For this reason, it is preferable that an appropriate amount of the targeting template nucleic acid introduced be a sufficient amount with the amount that does not cause random integrations at a high frequency as a limit.

In knock-in methods according to the present invention, cells that has been knocked in can be obtained with a high efficiency by subjecting a smaller number of moles of the selection template nucleic acid, compared to any of the nuclease template nucleic acid, the gRNA template nucleic acid or the gRNA, and the targeting template nucleic acid to the transfection step (1), and by only selecting the cell expressing the selectable marker in the selection step (2) (see Examples).

According to a certain aspect of the present invention, it is preferable that the number of moles (C) of the selection template nucleic acid be smaller than any of the number of moles (A) of the nuclease template nucleic acid and the number of moles (B) of the guide RNA template nucleic acid or the guide RNA. In the present invention, by making the number of moles (C) of the selection template nucleic acid subjected to the transfection step (1) at a particular ratio to the total number of moles (A+B+C) of the introduction nucleic acids, cells in which a target site has been modified with a higher efficiency can be obtained. In a certain embodiment, the ratio of the number of moles (C) of the selection template nucleic acid to the total number of moles of the introduction nucleic acids (C/(A+B+C)) is about $1/400$ to $1/10$, preferably about $1/200$ to $1/5$, and more preferably about $1/150$.

For a further preferred embodiment, a value (hereinafter, also referred to as a "Factor value") obtained by multiplying the number of moles (C) of the selection template nucleic acid by the number of types of the introduction nucleic acids and dividing the resultant value with the total number of moles of the introduction nucleic acids can be set at a particular ratio.

The Factor value is defined as the ratio of the number obtained by multiplying the number of moles (C) of the selection template nucleic acid by the number of types (n) of the introduction nucleic acids to the total (A+B+C) of the number of moles (A) of the nuclease template nucleic acid, the number of moles (B) of the guide RNA template nucleic acid or the guide RNA, and the number of moles (C) of the selection template nucleic acid (C×n/(A+B+C)).

$$\text{Factor value} = (C \times n/(A+B+C))$$

The Factor value can be 0.01 to 0.8, preferably 0.02 to 0.4, more preferably 0.02 to 0.2, and particularly preferably 0.02 to 0.04.

Cells selected in the selection step (2) are thought to be those capable of expressing a sufficient amount of selectable markers even when a small amount of the selection template nucleic acid was subjected to the transfection step (1). That is, there may be a possibility that the cells selected in the selection step (2) are those with a high uptake efficiency of the selection template nucleic acid, or those with a high expression efficiency of the selection template nucleic acid taken up. Accordingly, in these cells, a possibility was thought that: any of the uptake efficiency and the expression efficiency of the nuclease template nucleic acid, and the gRNA template nucleic acid or the gRNA is high; factors necessary for the knock-in via HR can be sufficiently expressed; and the targeting template nucleic acid, which has been introduced in a certain amount, is hard to be in an excessive amount compared to the amount of the RNA-guided nuclease and the gRNA expressed. As a result, in these cells, if the targeting template nucleic acid is introduced such that the amount thereof is not liable to be too little compared to the amount of the RNA-guided nuclease and the gRNA expressed, then a high knock-in efficiency can be obtained while suppressing both of the gene disruption and the random integration.

In the present invention, it is preferable that the introduction nucleic acids subjected to the transfection step (1) be introduced into a cell as respective, separate template nucleic acids or guide RNA. For example, when vectors are used for the introduction nucleic acids to introduce the template nucleic acids of (a) to (d), it is preferable that any of the nucleic acid sequence encoding an RNA-guided nuclease, the nucleic acid sequence encoding a guide RNA, the exogenous nucleic acid sequence, and the nucleic acid sequence encoding a selectable marker be not included in the same vector and be included in a separate vector.

The method of the present invention can be applied to either of knock-in and knockout genetic modifications, and it is preferable that the method be applied to knock-in (knock-in methods).

According to a certain aspect of the present invention, it is preferable that the number of moles (C) of the selection template nucleic acid be smaller than any of the number of moles (A) of the nuclease template nucleic acid, the number of moles (B) of the guide RNA template nucleic acid or the guide RNA, and the number of moles (D) of the targeting template nucleic acid. In the present invention, by making the number of moles (C) of the selection template nucleic acid subjected to the transfection step (1) at a particular ratio to the total number of moles (A+B+C+D) of the introduction nucleic acids, cells in which a target site has been modified with a higher efficiency can be obtained. In a certain embodiment, the ratio of the number of moles (C) of the selection template nucleic acid to the total number of moles of the introduction nucleic acids (C/(A+B+C+D)) is about 1/400 to 1/10, preferably about 1/200 to 1/5, and more preferably about 1/150.

For a further preferred embodiment, a value (hereinafter, also referred to as a "Factor value") obtained by multiplying the number of moles (C) of the selection template nucleic acid by the number of types of the introduction nucleic acids and dividing the resultant value with the total number of moles of the introduction nucleic acids can be set at a particular ratio.

The Factor value is defined as the ratio of the number obtained by multiplying the number of moles (C) of the selection template nucleic acid by the number of types (n) of the introduction nucleic acids to the total (A+B+C+D) of the number of moles (A) of the nuclease template nucleic acid, the number of moles (B) of the guide RNA template nucleic acid or the guide RNA, the number of moles (C) of the selection template nucleic acid, and the number of moles (D) of the targeting template nucleic acid (C×n/(A+B+C+D)).

Factor value=$(C \times n/(A+B+C+D))$

The Factor value can be 0.01 to 0.8, preferably 0.02 to 0.4, more preferably 0.02 to 0.2, and particularly preferably 0.02 to 0.04.

In reference to the "types of the introduction nucleic acids," in the present invention, introduction nucleic acids that can be regarded as the same type are those having a completely matched nucleic acid sequence. Accordingly, a template nucleic acid and a gRNA are separate types of the introduction nucleic acids.

Moreover, among template nucleic acids, a nuclease template nucleic acid, a gRNA template nucleic acid, a selection template nucleic acid, and a targeting template nucleic acid have nucleic acid sequences different from each other, and are therefore separate types of the introduction nucleic acids. However, when any two or more of a nuclease template nucleic acid, a gRNA template nucleic acid, a selection template nucleic acid, and a targeting template nucleic acid are combined to form one template nucleic acid, that combined template nucleic acid is counted as one type.

Furthermore, for example, a template nucleic acid comprising a nucleic acid sequence encoding a Cas9 nuclease and a template nucleic acid comprising a nucleic acid sequence encoding a Cas9 nickase comprise, although both are a nuclease template nucleic acid, nucleic acid sequences different from each other, and are therefore separate types of the introduction nucleic acids. Moreover, a template nucleic acid comprising a nucleic acid sequence encoding a domain of a Cas9 nuclease and a template nucleic acid comprising a nucleic acid sequence encoding another domain of the Cas9 nuclease also comprise nucleic acid sequences different from each other, and are therefore separate types of the introduction nucleic acids.

Similarly, the above also applies to a gRNA template nucleic acid, a selection template nucleic acid, and a targeting template nucleic acid, and all template nucleic acids with gRNAs included in nucleic acid sequences of template nucleic acids, nucleic acid sequences of selection markers or exogenous nucleic acid sequences different from each other are separate types of the introduction nucleic acids. Moreover, when a template nucleic acid has a nucleic acid sequence other than the nucleic acid sequence of a nuclease, a gRNA, a selection marker or an exogenous nucleic acid sequence (for example, a promoter sequence, etc.), like in a case where a template nucleic acid is, for example, a plasmid vector, all template nucleic acids with these nucleic acid sequences different from each other are separate types of the introduction nucleic acids.

The present invention relates to, from a certain point of view, a method of efficiently obtaining a desired cell in which a target site in the genome has been modified by using two or more "types of the introduction nucleic acids" (provided that at least one of them is an introduction nucleic acid comprising a selection template nucleic acid) and by making the number of moles of the selection template nucleic acid used at the transfection smaller than template nucleic acids included in the other introduction nucleic acids. The "types of the introduction nucleic acids" used at the transfection are just required to be two or more, and examples of "cases where two or more types of the introduction nucleic acids are used at the transfection" include a case where introduction nucleic acids comprising (i) a selection template nucleic acid and (ii) other nucleic acids are used, and include, in particular, a case where introduction nucleic acids comprising (i) a selection template nucleic acid and (ii) a targeting template nucleic acid are used, or a case where introduction nucleic acids comprising (i) a selection template nucleic acid and (ii) a nuclease template nucleic acid and a gRNA template nucleic acid are used.

The number of moles (C) of the selection marker template nucleic acid used at the transfection is smaller than the number of moles of any template nucleic acid or guide RNA used at the transfection. In the present invention, by making the number of moles (C) of the selection template nucleic acid subjected to the transfection step (1) at a particular ratio to the total number of moles (T) of the introduction nucleic acids, cells in which a target site has been modified with a higher efficiency can be obtained. In a certain embodiment, examples of preferred ranges of the ratio of the number of moles (C) of the selection template nucleic acid to the total number of moles of the introduction nucleic acids (C/T) include a similar range as C/(A+B+C+D) described above.

For a further preferred embodiment, a value (hereinafter, also referred to as a "Factor value") obtained by multiplying the number of moles (C) of the selection template nucleic acid by the number of types of the introduction nucleic acids (n') and dividing the resultant value with the total number of moles (T) of the introduction nucleic acids can be set at a particular ratio, and examples of preferred ranges of such value include a similar range as C×n/(A+B+C+D) described above.

The "types of the introduction nucleic acids" in the present invention are preferably three or more.

For example, when a Cas9 nuclease template nucleic acid, a gRNA template nucleic acid, a puromycin selection template nucleic acid, and a targeting template nucleic acid are used as introduction nucleic acids and they are not combined to each other to form separate template nucleic acids, the number of types of the introduction nucleic acids is four. When the Cas9 nuclease template nucleic acid and the gRNA template nucleic acid are combined to form one template nucleic acid, the number of types of the introduction nucleic acids will be three.

As described above, it is preferable that the introduction nucleic acids subjected to the transfection step (1) be introduced into a cell as respective, separate template nucleic acids or guide RNA. For example, when plasmid vectors are used for the introduction nucleic acids to introduce the template nucleic acids of (a) to (d), the nucleic acid sequence encoding an RNA-guided nuclease, the nucleic acid sequence encoding a guide RNA, the exogenous nucleic acid sequence, and the nucleic acid sequence encoding a selectable marker will be included in separate, four types of plasmid vectors. In this case, the Factor value is calculated from the formula: (C×4/(A+B+C+D)), described above.

[Cell]

A cell is not particularly limited as long as it is a eukaryotic cell, and it may be, for example, a yeast, a fungus, a protist, a plant cell, an insect cell, an amphibian cell, a reptilian cell, an avian cell, a non-human mammalian cell, or a human cell. Examples of non-human mammalian animals include a mouse, a rat, a hamster, a guinea pig, a rabbit, a dog, a cat, a pig, a cow, a horse, a sheep, and a monkey. The cell may be a cultured cell (in vitro and ex vivo).

In this description, "in vitro" means performing operations, such as transfection, to the cell described above and the like in a test tube or an incubator. On the other hand, in this description, "ex vivo" means taking out an organ, a cell and the like from an organism, and performing operations, such as transfection, to the cell and the like taken out.

The cell may be a pluripotent stem cell.

The pluripotent stem cell refers to an "embryonic stem cell" (ES cell), and a cell potentially having differentiation pluripotency similar to this, that is, an ability of differentiating into various tissues of an organism (all of endoderm, mesoderm and ectoderm). Examples of cells having a similar differentiation pluripotency as the ES cell include an "induced pluripotent stem cell" (in this description, also referred to as an "iPS cell").

The "induced pluripotent stem cell" refers to a cell obtained by introducing a certain factor (nuclear reprogramming factor) into a mammalian somatic cell or an undifferentiated stem cell to perform reprogramming. At present, there are various "induced pluripotent stem cells," and those that can also be used are as follows: an iPS cell established by Yamanaka, et al., by introducing four factors, Oct3/4, Sox2, Klf4 and c-Myc into a mouse fibroblast (Takahashi K, Yamanaka S., Cell, (2006) 126: 663-676); as well as an iPS cell derived from a human cell established by introducing the same four factors to a human fibroblast (Takahashi K, Yamanaka S., et al. Cell, (2007) 131: 861-872.); a Nanog-iPS cell established by introducing the four factors described above and then performing screening with the expression of Nanog as an indicator (Okita, K., Ichisaka, T., and Yamanaka, S. (2007). Nature 448, 313-317.); an iPS cell produced with a method in which c-Myc is not included (Nakagawa M, Yamanaka S., et al. Nature Biotechnology, (2008) 26, 101-106); and an iPS cell established by introducing six factors with a virus free method (Okita K et al. Nat. Methods 2011 May; 8(5):409-12, Okita K et al. Stem Cells. 31(3):458-66.). In addition, an induced pluripotent stem cell, produced by Thomson, et al., established by introducing four factors, OCT3/4, SOX2, NANOG and LIN28 (Yu J., Thomson J A. et al., Science (2007) 318: 1917-1920.), an induced pluripotent stem cell produced by Daley, et al. (Park I H, Daley G Q. et al., Nature (2007) 451: 141-146), and an induced pluripotent stem cell produced by Sakurada, et al. (Japanese Patent Application Laid-Open No. 2008-307007), etc. can also be used.

Besides, any of the induced pluripotent stem cells known in the art described in all published papers (for example, Shi Y., Ding S., et al., Cell Stem Cell, (2008) Vol3, Issue 5, 568-574; Kim J B., Scholer H R., et al., Nature, (2008) 454, 646-650; Huangfu D., Melton, D A., et al., Nature Biotechnology, (2008) 26, No 7, 795-797), or patents (for example, Japanese Patent Application Laid-Open No. 2008-307007, Japanese Patent Application Laid-Open No. 2008-283972, US2008-2336610, US2009-047263, WO2007-069666, WO2008-118220, WO2008-124133, WO2008-151058, WO2009-006930, WO2009-006997, WO2009-007852) can be used.

As an induced pluripotent cell line, every kind of iPS cell line established by NIH, Riken, Kyoto University, etc. is available. For example, examples of human iPS cell lines include line HiPS-RIKEN-1A, line HiPS-RIKEN-2A, line HiPS-RIKEN-12A and line Nips-B2 of Riken, line 253G1, line 201B7, line 409B2, line 454E2, line 606A1, line 610B1 and line 648A1 of Kyoto University, etc.

[RNA-Guided Nuclease]

Examples of RNA-guided nucleases used in the present invention include, for example, an RNA-guided endonuclease.

The RNA-guided endonuclease comprises at least one nuclease domain and at least one domain interacting with a gRNA. The RNA-guided endonuclease is guided to a target site of the genome by the gRNA.

The RNA-guided endonuclease may be derived from Clustered Regularly Interspersed Short Palindromic Repeats (CRISPR)/CRISPR-associated (Cas) system. The CRISPR/Cas system can be a type I, a type II or a type III system. Non-limiting examples of appropriate CRISPR/Cas proteins include Cas3, Cas4, Cas5, Cas5e (or CasD), Cas6, Cas6e, Cas6f, Cas7, Cas8a1, Cas8a2, Cas8b, Cas8c, Cas9, Cas10, Cas10d, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4 and Cu1966.

In one aspect, the RNA-guided endonuclease is derived from a type II CRISPR/Cas system. In a particular aspect, the RNA-guided endonuclease is derived from a Cas9 protein. The Cas9 protein may be derived from *Streptococcus pyogenes, Streptococcus thermophilus*, the genus *Streptococcus, Staphylococcus aureus*, the genus *Staphylococcus, Nocardiopsis dassonvillei, Streptomyces pristinaespiralis, Streptomyces viridochromogenes, Streptosporangium roseum, Alicyclobacillus acidocaldarius, Bacillus pseudomycoides, Bacillus selenitireducens, Exiguobacterium sibiricum, Francisella novicida, Lactobacillus delbrueckii, Lactobacillus salivarius, Microscilla marina, Bur-* kholderia bacteria, Polaromonas naphthalenivorans, Polaromonas spp., Crocosphaera watsonii, the genus *Cyanothece, Microcystis aeruginosa*, the genus *Synechococcus, Acetohalobium arabaticum, Ammonifex degensii, Caldicellulosiruptor becscii, Campylobacter jejuni, Campylobacter coli, Neisseria meningitides, Candidatus desulforudis, Clostridium botulinum, Clostridium difficile, Finegoldia magna, Natranaerobius thermophilusm, Pelotomaculum thermopropionicum, Acidithiobacillus caldus, Acidithiobacillus ferrooxidans, Allochromatium vinosum*, the genus *Marinobacter, Nitrosococcus halophilus, Nitrosococccus watsoni, Pseudoalteromonas haloplanktis, Ktedonobacter racemifer, Methanohalbium evestigatum, Anabaena variabilis, Nodularia spumigena*, the genus *Nostoc, Arthrospira maxima, Arthrospira platensis*, the genus *Arthrospira*, the genus *Lyngbya, Microcoleus chthonoplastes*, the genus *Oscillatoria, Petrotoga mobilis, Thermosipho africanus*, or *Acaryochloris marina*.

The CRISPR/Cas protein may be a wild-type CRISPR/Cas protein, a modified CRISPR/Cas protein, or a fragment of a wild-type or modified CRISPR/Cas protein. The CRISPR/Cas protein may be modified in order to increase the nucleic acid binding affinity and/or specificity, to change the enzymatic activity, or to change another property of the protein.

The RNA-guided nuclease may be a Cas nuclease or a Cas nickase. Here, the Cas nuclease or the Cas nickase refers to a protein component essential for the CRISPR/Cas system, and means an endonuclease or a nickase having an activity when combined with two RNAs, referred to as a CRISPR RNA (crRNA) and a transactivating crRNA (tracrRNA), to form a composite. The nickase refers to a DNA nicking enzyme, in which a nick is present in only one of DNA strands. Generally, the Cas9 protein comprises at least two nuclease (that is, DNase) domain. For example, the Cas9 protein may comprise a RuvC-like nuclease domain and an HNH-like nuclease domain. The RuvC and HNH domains cooperate together to cleave a single strand, in order to cleave the double strand in DNA (Jinek et al., Science, 337: 816-821). In a certain aspect, a protein derived from Cas9 may be modified to comprise only one functional nuclease domain (either of the RuvC-like or HNH-like nuclease domain). For example, the protein derived from Cas9 may be modified in such a way that one of the nuclease domains is deleted or mutated such that it no longer functions (that is, there is no nuclease activity). In an aspect where one of the nuclease domains is inactive, although the protein derived from Cas9 can introduce a nick into the double stranded nucleic acid, but it cannot cleave the double stranded DNA. For example, a conversion of aspartic acid to alanine at the RuvC-like domain (D10A) converts the protein derived from Cas9 into a nickase. Similarly, a conversion of histidine to alanine at the HNH domain (H840A or H839A) converts the protein derived from Cas9 into a nickase. Each nuclease domain can be modified using well-known methods, such as a site-directed mutagenesis method, a PCR-mediated mutagenesis method, and total gene synthesis, as well as other methods known in the art.

For the RNA-guided nuclease, in particular, a Cas nuclease or a Cas nickase derived from bacteria of the genus *Streptococcus* (*Streptococcus* sp.), bacteria of the genus *Staphylococcus* (*Staphylococcus* sp.), *Francisella novicida* or *Campylobacter jejuni* can be used. Among these, as an origin, *Streptococcus pyogenes* (*S. pyogenes*) is preferred in bacteria of the genus *Streptococcus*, and *Staphylococcus aureus* (*S. aureus*) is preferred in bacteria of the genus *Staphylococcus*. The Cas9 nuclease or the Cas9 nickase derived from *Streptococcus pyogenes* and *Staphylococcus aureus* recognizes NGG or NAG trinucleotide.

Moreover, in a particular aspect, the RNA-guided endonuclease may be Cpf1 (CRISPR from *Prevotella* and *Francisella*), which has been relatively recently identified as a type V system. A Cpf1 protein may be derived from *Acidaminococcus* sp., and Lachnospiraceae bacterium or *Francisella novicida*.

Furthermore, instead of the RNA-guided nuclease, a site-specific nuclease, such as a Zinc finger nuclease (ZFN) or a transcriptional activator-like effector nuclease (TALEN) may also be used.

In a method of modifying a target site in the genome of a eukaryotic cell, according to this embodiment, introduction nucleic acids are introduced into the cell in the transfection step (1), the introduction nucleic acids comprising: a template nucleic acid (nuclease nucleic acid) comprising a nucleic acid sequence encoding a site-specific nuclease (for example, referred to as TALEN1) that cleaves a certain site in the genome; a template nucleic acid (nuclease nucleic acid) comprising a nucleic acid sequence encoding a site-specific nuclease (for example, referred to as TALEN2) that cleaves another site; and a template nucleic acid (selection template nucleic acid) comprising a nucleic acid sequence encoding a selectable marker. In this case, the number of moles of the selection template nucleic acid is just required to be smaller than the number of moles of the nuclease template nucleic acid (the total of the number of moles of TALEN1 and TALEN2 when they are separate template nucleic acids). Furthermore, when a targeting template nucleic acid is used in the transfection step (1), the number of moles of the selection template nucleic acid is made smaller than the number of moles of the targeting template nucleic acid.

In summary, in the method of modifying a target site in the genome of a eukaryotic cell, according to this embodiment, the number of moles of the selection template nucleic acid is also made smaller than any of the number of moles of the introduction nucleic acids other than the selection template nucleic acid, and a Factor value in this embodiment may also be defined as the ratio of the number obtained by multiplying the number of moles of the selection template nucleic acid by the number of types (n) of the introduction nucleic acids to the total number of moles of the introduction nucleic acids, in the same way as described above.

[gRNA]

A gRNA is specific to a target site in the genome, and it is just required to be an RNA that can form a composite with an RNA-guided nuclease and bring the RNA-guided nuclease to the target site in the genome. The gRNA is constituted by two RNAs, that is, a CRISPR RNA (crRNA) and a transactivating crRNA (tracrRNA), and the crRNA comprises a part complementary to the target site in the genome. The gRNA may be a chimeric RNA comprising a crRNA and a tracrRNA, and may be a single stranded RNA (sgRNA) produced by fusion of essential parts of the crRNA and the tracrRNA.

When the transfection is performed in the eukaryotic cell, the gRNA may be a chimeric RNA comprising a crRNA and a tracrRNA, and preferably is a single stranded RNA (sgRNA) produced by fusion of essential parts of the crRNA and the tracrRNA.

The gRNA comprises three regions: a first region in the 5'-end complementary to a target site in a chromosome sequence; a second interior region forming a stem loop structure; and a third 3'-region essentially remaining as a single strand. The first region varies from gRNA to gRNA such that a gRNA guides an RNA-guided nuclease to a particular target site. The second and third regions of the gRNA may be the same in all gRNAs.

The first region is complementary to the sequence at the target site to form base pairs with the target site in the genome. The first region may comprise from about 10 nucleotides to about 25 or more nucleotides. For example, the base-paring region between the first region and the target site in the genome may have a nucleotide length of 10, 11, 12, 13, 14, 15, 16, 17, 18, 19, 20, 22, 23, 24, 25, or 25 or more. In an exemplary aspect, the first region has a nucleotide length of 19, 20 or 21.

The gRNA comprises the second region forming a secondary structure. The secondary structure may comprise a stem (or hairpin) and a loop. The length of the loop and the stem is variable. The second region may have a range of the nucleotide length of from about 16 to about 60. In an exemplary aspect, the loop has a nucleotide length of about 4 and the stem comprises about 12 base pairs.

The length of the stem (or hairpin) and the loop is preferably from about 20 to about 80 nucleotides in length, and more preferably from about 30 to about 50 nucleotides.

The gRNA comprises the third region essentially remaining as a single strand at the 3'-end. The third region does not have complementarity to the chromosome sequence in the cell of interest, and does not have complementarity to the remaining part of the gRNA. The length of the third region is variable. Generally, the third region has a nucleotide length of about 4 or more. For example, the length of the third region has a range of the nucleotide length of from about 5 to about 60.

The combined length of the second and third regions may have a range of the nucleotide length of from about 30 to about 120. The combined length of the second and third regions preferably has a range of the nucleotide length of from about 70 to about 100.

[Selectable Marker (Selection Marker)]

A selectable marker (selection marker) is a polypeptide that enables distinguishment between cells that express and do not express the selectable marker, and may be, for example, a fluorescent protein, an enzyme that catalyzes a color reaction and/or a luminous reaction, a drug resistance factor or the like. As the fluorescent protein, for example, a green fluorescent protein (GFP), a cyan fluorescent protein (CFP), a yellow fluorescent protein (YFP) and a red fluorescent protein (dsRed) and the like may be used. As the enzyme that catalyzes a color reaction and/or a luminous reaction, for example, luciferase, β-glucuronidase (GUS) and β-galactosidase (lacZ) and the like may be used. As the drug resistance factor, for example, resistance factors to antibiotics, such as puromycin, neomycin, hygromycin, G418 and blasticidin, are known.

From the viewpoint of ease of handling and selectivity, etc., the selectable marker is preferably a drug resistance factor, and particularly preferably a puromycin resistance factor. On the other hand, from the viewpoint of ease and accuracy in the evaluation of the knock-in efficiency, etc., fluorescent protein and an enzyme that catalyzes a color reaction and/or a luminous reaction are preferred, and a fluorescent protein is more preferred.

[Introduction Nucleic Acids]

Introduction nucleic acids in the present invention mean nucleic acids introduced into a cell, and comprise a guide RNA and a template nucleic acid.

[Template Nucleic Acid]

A template nucleic acid in the present invention means a nucleic acid that serves as a template when other molecules are produced, and examples include a DNA (for example, oligoDNA), an RNA (for example, oligoRNA), and a nucleic acid, a vector and the like that comprises at least one of them. The template nucleic acid in the present invention refers to, more particularly, a nuclease template nucleic acid, a gRNA template nucleic acid, a selection template nucleic acid, and a targeting template nucleic acid.

For these template nucleic acids, different types may be used. For example, it is possible that a gene expression vector is used for the nuclease template nucleic acid, the selection template nucleic acid and the gRNA template nucleic acid, and a nucleic acid comprising an oligoDNA is used for the targeting template nucleic acid.

Vectors in the present invention include, for example, a plasmid vector, a phagemid, a cosmid, an artificial chromosome/minichromosome, a transposon, and a virus vector (for example, a lentivirus vector, an adeno-associated virus vector, etc.). The vector is preferably a plasmid vector, and non-limiting examples of the types of suitable plasmid vectors include pUC, pBR322, pET, pBluescript, and variants thereof. The vector may further comprise an expression regulatory sequence (for example, an enhancer sequence, a Kozak sequence, a polyadenylation sequence, a transcriptional termination sequence, etc.), a selection marker (for example, a drug resistance factor described above, etc.) sequence, an origin of replication, and the like. Note that, in this description, a vector may be particularly referred to as a "gene expression vector," into which a nucleic acid sequence encoding a protein, an RNA, a factor and the like desired to be expressed in a cell into which the nucleic acid sequence is introduced is incorporated under the control of a promoter.

Examples of promoters include, for example, a cytomegalovirus (CMV) immediate early promoter, a simian virus (SV40) promoter, an adenovirus major late promoter, a rous sarcoma virus (RSV) promoter, a mouse mammary tumor virus (MMTV) promoter, a phosphoglycerate kinase (PGK) promoter, an elongation factor (ED1)-α promoter, a ubiquitin promoter, an actin promoter, a tubulin promoter, an immunoglobulin promoter, a fragment thereof, or a combination of any of those described above. The promoter sequence may be wild-type, or may be modified for a more efficient expression.

For the template nucleic acid in the present invention, it is preferable to use a plasmid vector.

[Nuclease Template Nucleic Acid and Selection Template Nucleic Acid]

A nuclease template nucleic acid and a selection template nucleic acid may be those in which a nucleic acid sequence encoding an RNA-guided nuclease or a nucleic acid sequence encoding a selection marker is incorporated into a generic gene expression vector. The nucleic acid sequence encoding an RNA-guided nuclease and the nucleic acid sequence encoding a selection marker are incorporated under the control of a generic promoter.

The nucleic acid sequence encoding an RNA-guided nuclease and the nucleic acid sequence encoding a selection marker may be a codon optimized for being efficiently translated into a protein in a eukaryotic cell of interest. For example, the codon may be optimized for expression in a human, a mouse, a rat, a hamster, a cow, a pig, a cat, a dog, a fish, an amphibian, a plant, a yeast, an insect, etc. Optimization of the codon can be performed according to methods known to those skilled in the art.

[gRNA Template Nucleic Acid or gRNA]

A gRNA may be introduced into a cell in a form of an RNA (gRNA) or in a form of an RNA template nucleic acid (for example, a DNA encoding a gRNA). In the present invention, the gRNA is preferably introduced in a form of a gRNA template nucleic acid, and more preferably introduced as a gRNA template nucleic acid (gRNA vector) in which a nucleic acid sequence encoding a gRNA is incorporated into a generic gene expression vector. When a gRNA vector is used, the nucleic acid sequence encoding a gRNA is incorporated under the control of a generic promoter.

A nucleic acid sequence encoding an RNA-guided nuclease and a nucleic acid sequence encoding a gRNA may be incorporated under the control of different promoters in the same template nucleic acid to form one template nucleic acid comprising a nuclease template nucleic acid and a gRNA template nucleic acid, but from the viewpoint of improving the knock-in and/or knockout efficiency, it is preferable that they be separate template nucleic acids.

[Targeting Template Nucleic Acid]

As a targeting template nucleic acid, an oligoDNA and a generic vector, etc. comprising an exogenous nucleic acid sequence can be used, and a plasmid vector comprising an exogenous nucleic acid sequence is preferred. The exogenous nucleic acid sequence can be a sequence not naturally present in a cell, or a sequence present at a position different from its natural position in the cellular genome. For example, by inserting the exogenous nucleic acid sequence into the genome, it becomes possible to express a protein encoded by a sequence included in the inserted exogenous nucleic acid sequence. Moreover, when a sequence included in the inserted exogenous nucleic acid sequence encodes a termination codon, it becomes possible to suppress production of a protein that is expressed under natural conditions. The exogenous nucleic acid sequence may comprise a protein coding sequence incorporated under the control of an exogenous promoter. Alternatively, the exogenous nucleic acid sequence may be incorporated into a chromosome sequence such that its expression may be controlled by an endogenous promoter.

Furthermore, the exogenous nucleic acid sequence can be a sequence that may be substantially the same as a natural sequence of the chromosome at a target site or its proximal location, but comprises at least one nucleotide change. The nucleotide change may be, for example, an insertion, a deletion, a substitution or an addition of one or more nucleotide, or a combination thereof. Accordingly, the cell can produce a modified gene product from the chromosome sequence at the target site.

A targeting vector has a structure in which a targeting cassette, which includes an exogenous nucleic acid sequence to be inserted, is flanked by two homology arms for causing HR. The homology arms each have a sequence that is substantially the same as the sequence located upstream or downstream of the target site of the chromosome. Here, a "sequence that is substantially the same" means a sequence having a sequence identity of at least about 75%. Thus, the homology arms have a sequence identity of 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% with the sequence upstream or downstream of the target site. The sequence identity is preferably at least 85% or 90%, more preferably at least 95% or 97%, and particularly preferably at least 99%.

The term "sequence identity" means a percentage (%) of matched base pairs between two gene sequences when these two sequences are aligned such that the match of the base pairs becomes maximum.

The sequence identity can be determined according to any method known to those skilled in the art. For example, it can be determined with the use of Clustal, a multiple sequence alignment program by Higgins et al. (Gene 73, 1, 237-244, 1988). The Clustal program is available on the Internet, for example, at the website of European Bioinformatics Institute (EBI).

The homology arms may have a range of the length of from 20 nucleotides to 5000 nucleotides. The homology arms may comprise 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2800, 3000, 3200, 3400, 3600, 3800, 4000, 4200, 4400, 4600, 4800, or 5000 nucleotides. The homology arms may preferably have a range of the length of from 50 to 1500 nucleotides, more preferably the length of from 500 to 1500 nucleotides, and particularly preferably the length of from 700 to 1000 nucleotides.

The targeting cassette may comprise a nucleic acid sequence encoding a selection marker (for example, a drug resistance gene described above, etc.)

The targeting vector may be a plasmid vector.

[Transfection Step (1)]

In this description, transfection means an operation of bringing introduction nucleic acids into contact with a cell for the purpose of introducing the introduction nucleic acids into the cell. Moreover, in this description, the introduction of the introduction nucleic acids into the cell means that the introduction nucleic acids brought into contact with the cell by the transfection are incorporated into the cell.

The introduction nucleic acids comprising a nuclease template nucleic acid, a gRNA template nucleic acid or gRNA, a targeting template nucleic acid, a selection template nucleic acid and the like are transfected simultaneously or successively. The transfection can be performed by conventionally known approaches, and for example, microinjection, electroporation, DEAE-dextran treatment, lipofection, nanoparticle-mediated transfection, etc. can be applied. By these approaches, the introduction nucleic acids can be introduced into the cell. For example, according to the electroporation, an appropriate voltage is applied to a buffer solution including a cell to which introduction nucleic acids are applied, thereby allowing the introduction nucleic acids to pass through the cell membrane and to be introduced into the cell. As another example, according to the lipofection, by applying a complex of a lipid molecule and of introduction nucleic acids to a cell, the complex is allowed to pass through the cell membrane and the introduction nucleic acids are introduced into the cell. As described above, an approach for the transfection in the present invention is not particularly limited, and can be, for example, an approach similar to those described in Nature Protocols (K. Yusa et al., vol. 8, No. 10, 2013, 2061-2078), Nature Protocols (T. Sakuma et al., vol. 11, No. 1, 2016, 118-133), Nature Protocols (B. Wefers et al., vol. 8, No. 12, 2013, 2355-2379), etc.

A cell into which introduction nucleic acids are introduced is incubated for an appropriate period of time. By incubating the cell for an appropriate period of time, a cell in which factors necessary for modification of a target site in the genome, such as a nuclease, a gRNA and a selection marker, have been expressed can be obtained. Moreover, in the case of a knock-in method, a cell into which an exogenous nucleic acid sequence has been inserted can be obtained. The incubation period is not particularly limited, and can be about 24 to 72 hours and is preferably about 24 to 48 hours. The incubation conditions may be at a temperature of about 37° C. under the presence of 5% $CO_2$. The culture medium is appropriately selected depending on the type of the cell.

[Selection Step (2)]

In this step, a cell expressing a selection marker is selected.

When a drug resistance factor is used as the selection marker, the selection of the cell can be performed by culturing a cell after the transfection step (1) under the presence of a drug, and obtaining only a cell that has acquired drug resistance as a living cell. In addition, for example, when a fluorescent protein is used as the selection marker, the selection of the cell can be performed by identifying and collecting a cell showing fluorescence using a fluorescence microscope, a fluorescence intensimeter, a flow cytometer or the like with regard to a cell after the transfection step (1).

As for the drug concentration in a culture medium in a case where a cell is incubated under the presence of the drug, the drug concentration is appropriately selected depending on the type of the drug, and can be a concentration in which a cell that has acquired drug resistance survives and a cell that has not acquired drug resistance dies out. More particularly, for example, when a puromycin resistance factor is introduced, the concentration of puromycin can be from 0.02 to 4 µg/mL, and is preferably about 1 µg/mL. When a hygromycin resistance factor is introduced, the concentration of hygromycin can be from 50 to 1000 µg/mL, and is preferably about 400 µg/mL. The incubation conditions may be at a temperature of about 37° C. under the presence of 5% $CO_2$. The culture medium is appropriately selected depending on the type of the cell used.

In addition, when a nucleic acid sequence encoding a selection marker (for example, a drug resistance gene described above, etc.) is also included in the targeting cassette of the targeting template nucleic acid, the selection of the cell using the expression of said selection marker as an indicator may be performed as well. In this case, the selection marker expressed by the selection template nucleic acid and the selection marker expressed by the targeting template nucleic acid can be different from each other, and for example, a combination of a puromycin resistance factor and of a neomycin resistance factor can be utilized as drug resistance factors. By using two types of selection markers in combination, in reference to a target site in the genome, the ratio of knock-in at homoallele can be increased compared to the knock-in at heteroallele.

By incubating a cell subjected to the transfection step (1) under the presence of the drug at a concentration described above, a cell that has acquired drug resistance can be selected. The incubation period under the presence of the drug is appropriately selected depending on the type of the drug. For example, in the case of puromycin, the incubation period can be 2 days or more, and can be preferably about 3 to 14 days. In the case of hygromycin, the incubation period can be 5 days or more, and can be preferably about 7 to 14 days. In the case of neomycin, the incubation period can be 7 days or more, and can be preferably about 10 to 20 days.

The selection step for a cell by a selection marker is not particularly limited, and for example, an approach similar to those described in StemCells (C. Ren et al., vol. 24, 2006, 1338-1347), Biochem. Biophysic. Res. Com. (A. Kubosaki et al., vol. 426, 2012, 141-147), Cancer Res. (I. Yamato et al., vol. 72, No. 18, 2012, 4829-4839), etc. can be used.

2. Method for Detecting Presence or Absence of Nucleic Acid Sequence to be Detected at Predetermined Locus on Chromosome A method of detecting the presence or absence of a nucleic acid sequence to be detected at a predetermined locus on a chromosome, according to the present invention (in this description, may be referred to as the "detecting method of the present invention"), essentially includes the following steps (2) and (3), and optionally includes a step (1).

(1) A step of preparing a genomic DNA fragment from a test cell.

(2) A step of detecting, via a digital PCR method, the presence or absence of hybridization, to a genomic DNA fragment derived from the chromosome, of a first probe nucleic acid that hybridizes to all or part of the nucleic acid sequence to be detected, and a second probe nucleic acid that hybridizes to a nucleic acid sequence other than the nucleic acid sequence to be detected in the predetermined locus.

(3) A step of detecting the presence of the nucleic acid sequence to be detected at the predetermined locus when the first probe nucleic acid and the second probe nucleic acid are hybridized to the genomic DNA fragment and double-positive is detected, and of detecting the absence of the nucleic acid sequence to be detected at the predetermined locus when double-positive is not detected.

Here, the term "locus" has the same meaning as a "position on the chromosome." The "locus" may be, not only at a gene region comprising a transcriptional regulatory region, but also at a non-gene region.

The "nucleic acid sequence to be detected" may be any, natural or artificial nucleic acid sequence. A natural nucleic acid sequence can include all of nucleic acid sequences of a transcriptional region/non-transcriptional region, and nucleic acid sequences of a protein coding region/non-coding region. In addition, the base length of the nucleic acid sequence to be detected may be arbitrary.

According to the detecting method of the present invention, it is also possible to know the ratio of cells in which a desired modification is produced in a cell sample subjected to the modification at a target site in the genome. In general, in order to obtain cells in which a desired modification is produced from the cell sample described above, (i) the cell sample is subjected to a limiting dilution method, etc. to perform monocloning, and then (ii) the genomic sequence in the monocloned cells is confirmed. When the ratio of cells in which a desired modification is produced in the cell sample is low, the possibility of being able to obtain (monocloned) cells in which the desired modification is produced during the confirmation in (ii) described above gets low. In order to efficiently obtain desired (monocloned) cells, it is desirable to know, before performing (i) described above, which requires long time, whether the cell sample includes cells in which the desired modification is produced at a high ratio sufficient for obtaining cells in which the desired modification is produced after monocloning. By applying the detecting method of the present invention to the cell sample described above, it is possible to know the ratio of cells in which the desired modification is produced in the cell sample, and therefore, a possibility of not being able to obtain desired cells in the end after performing each process of (i) and (ii) can be reduced.

Examples of the cell sample described above include, for example, eukaryotic cells to which the method of the present invention is applied.

In addition, the confirmation described in (ii) can be performed by applying the detecting method of the present invention to the cell sample described above.

[Genomic DNA Fragment Preparation Step (1)]

In this step, a genomic DNA fragment is prepared from a test cell. The preparation of a genomic DNA fragment from a test cell can be performed by conventionally known approaches (see, for example, Methods Enzymol., 2013, 529:161-169 and Nucleic Acids Res., 1988, 16(12):5698), and for example, can be performed using a commercially available kit comprising a spin column and a buffer based on a silica membrane method.

Through the extraction operation from the cell, the genomic DNA is fragmented to be genomic DNA fragments, normally with 1 kbp to 600 kbps and typically with about 50 to 100 kbps.

This step is not essential when genomic DNA fragments prepared in advance are used for the next process.

[Digital PCR Step (2)]

In this step, the presence or absence of hybridization, to a genomic DNA fragment, of a first probe nucleic acid that hybridizes to all or part of a nucleic acid sequence to be detected, and of a second probe nucleic acid that hybridizes to a nucleic acid sequence other than the nucleic acid sequence to be detected in a predetermined locus is detected via a digital PCR method.

The digital PCR method is an approach for detecting and quantifying nucleic acids, and is a well-known and generic approach in the art. In the digital PCR method, at first, a sample (limiting dilute solution of nucleic acids comprising a target nucleic acid) is introduced dividedly into numerous microreaction regions using a nanofluidic chip. In some of the microreaction regions, the target nucleic acid is introduced, while in the other microreaction regions, nucleic acids other than the target nucleic acid are included or no nucleic acid is included. Then, PCR reactions using a primer set that can amplify the target nucleic acid are performed in each microreaction region simultaneously. During the amplification, by using a pigment labeled probe that specifically hybridizes to the target nucleic acid, signals are detected (positive). When the target nucleic acid is not present in a microreaction region, no signal is detected in that microreaction region (negative). After the reaction, the absolute number of molecules of the target nucleic acid in the sample can also be calculated based on a signal positive/negative ratio in the microreaction regions. To a microreaction region that may include two or more target nucleic acids, a correction factor according to a Poisson model is applied.

By referring to FIG. 1, a first probe nucleic acid and a second probe nucleic acid subjected to the digital PCR method will be described.

FIG. 1(A) shows a nucleic acid sequence to be detected $T_1$ present at a locus $L_1$ on the genomic DNA fragment.

A first probe nucleic acid $P_1$ (hereinafter, simply referred to as "Probe $P_1$") has a nucleotide sequence complementary to all or part of the nucleic acid sequence to be detected $T_1$ and specifically hybridizes to the nucleic acid sequence to be detected $T_1$.

A second probe nucleic acid $P_2$ (hereinafter, simply referred to as "Probe $P_2$") has a nucleotide sequence complementary to a nucleic acid sequence other than the nucleic acid sequence to be detected $T_1$ in the locus $L_1$ and specifically hybridizes to that nucleic acid sequence.

Probe $P_1$ hybridizes to a nucleotide sequence within the nucleic acid sequence to be detected $T_1$ while Probe $P_2$ hybridizes to a nucleotide sequence outside of the nucleic acid sequence to be detected $T_1$, and therefore, in the locus $L_1$, a first region to which Probe $P_1$ can hybridize and a second region to which Probe $P_2$ can hybridize will be separated by a predetermined base length (distance d).

Here, the distance d is not particularly limited, but is about 0.1 kb to 100 kbs, preferably about 0.1 to 10 kbs, more preferably about 0.1 kb to 5 kbs, and further preferably about 0.1 kb to 2 kbs.

For Probes $P_1$ and $P_2$, commercially available probes (for example, TaqMan (R) probe) to which chemical modification and pigment labeling have been performed such that the hybridization of these probes to the complementary strand (target nucleic acid in the digital PCR method) can be optically detected may be used. For PCR reactions, primer sets that can amplify target nucleic acids of Probes $P_1$ and $P_2$ respectively are designed.

[Detection Step (3)]

In this step, the presence of the nucleic acid sequence to be detected $T_1$ is detected at the locus $L_1$ when Probe $P_1$ and Probe $P_2$ are hybridized to the genomic DNA fragment and double-positive is detected, and the absence of the nucleic acid sequence to be detected $T_1$ is detected at the locus $L_1$ when double-positive is not detected.

This will be described referring to FIG. 1.

In the first place, as shown in FIG. 1(A), when the nucleic acid sequence to be detected $T_1$ is present at the locus $L_1$ on the genomic DNA fragment, "double-positive" is detected in the digital PCR method, where both signals for Probe $P_1$ and Probe $P_2$ are positive.

On the other hand, when a microreaction region in which the signal for Probe $P_1$ is positive and a microreaction region in which the signal for Probe $P_2$ is positive are present, but a microreaction region in which double-positive is detected is not present in the digital PCR method, as shown in FIG. 1(B), it is revealed that the nucleic acid sequence to be detected $T_1$ is present at a locus $L_2$ that is on some genomic DNA fragment and does not have the second region to which Probe $P_2$ hybridizes. When the nucleic acid sequence to be detected $T_1$ is an endogenous nucleic acid sequence present at the locus $L_1$ in the wild-type chromosome, the absence of a microreaction region in which double-positive for Probe $P_1$ and Probe $P_2$ is detected reveals that said endogenous nucleic acid sequence has been translocated from its original locus $L_1$ to the locus $L_2$ or has been deleted from the chromosome in the test cell.

In addition, when only the signal for Probe $P_2$ is positive and the signal for Probe $P_1$ is negative in the digital PCR method, as shown in FIG. 1(C), it is revealed that the nucleic acid sequence to be detected $T_1$ is not present at the locus $L_1$ that has the second region to which Probe $P_2$ hybridizes and is not present on any of genomic DNA fragments. When the nucleic acid sequence to be detected $T_1$ is an endogenous nucleic acid sequence present at the locus $L_1$ in the wild-type chromosome, this reveals that said endogenous nucleic acid sequence has been deleted from the chromosome in the test cell.

Here, when an unexpected dividing of the chromosome (hereinafter, may also be simply referred to as "fragmentation") between the first region to which Probe $P_1$ can hybridize and the second region to which Probe $P_2$ hybridizes in the locus $L_1$ occurs during the genomic DNA fragment preparation step (1), this leads to false negative of "single positive 1" and "single positive 2." Methods of eliminating the influence of such fragmentation will be described in detail hereinafter.

3. Method of Evaluating Knock-in Efficiency

The method of detecting the presence or absence of a nucleic acid sequence to be detected at a predetermined locus on the chromosome according to the present invention can be applied to a method of evaluating the knock-in efficiency.

The method of evaluating the knock-in efficiency according to the present invention comprises the following steps.
(1) A step of preparing a genomic DNA fragment from a test cell or population thereof.
(2) A step of detecting, via a digital PCR method, the presence or absence of hybridization, to the genomic DNA fragment derived from a chromosome of the test cell, of
a first probe nucleic acid that hybridizes to all or part of an exogenous nucleic acid sequence contemplated to be inserted into, via genetic recombination, a locus of interest on the chromosome, and
a second probe nucleic acid that hybridizes to a nucleic acid sequence other than the exogenous nucleic acid sequence in the locus of interest that is not located between two homology arms subjected to the genetic recombination.
(3) A step of detecting the presence of the exogenous nucleic acid sequence at the locus of interest when the first probe nucleic acid and the second probe nucleic acid are hybridized to the genomic DNA fragment and double-positive is detected, and
of detecting the absence of the exogenous nucleic acid sequence at the locus of interest when double-positive is not detected.

Here, the "exogenous nucleic acid sequence" may be any nucleic acid sequence and its base length is also arbitrary.

In addition, an embodiment of detecting an exogenous nucleic acid sequence contemplated to be inserted into, via homologous recombination using homology arms, a locus of interest on a chromosome will be described here, but the exogenous nucleic acid sequence may be inserted into the locus of interest on the chromosome not according to the homologous recombination. As for approaches of inserting an exogenous nucleic acid sequence into a locus of interest on a chromosome not according to homologous recombination, for example, a method referred to as HITI (homology-independent targeted integration) (Nature, 2016, 540(7631): 144-149), a method referred to as ObLiGaRe (Obligate Ligation-Gated Recombination) (Genome Res. 2013, 23(3): 539-46) and the like are known. In this case, the second probe is a nucleic acid sequence in the locus of interest and is designed to hybridize to a nucleic acid sequence other than the exogenous nucleic acid sequence.

[Genomic DNA Fragment Preparation Step (1)]

In this step, a genomic DNA fragment is prepared from a test cell subjected to an operation for inserting an exogenous nucleic acid sequence into, via homologous recombination, a locus of interest on a chromosome. Details of this step are as already described.

In a case where the insertion percentage (knock-in efficiency) of an exogenous nucleic acid sequence into a locus of interest in a test cell is evaluated, a genomic DNA fragment is prepared from a cell population of the test cell.

[Digital PCR Step (2)]

In this step, the presence or absence of hybridization, to a genomic DNA fragment, of a first probe nucleic acid that hybridizes to all or part of an exogenous nucleic acid sequence, and of a second probe nucleic acid that hybridizes to a nucleic acid sequence other than the exogenous nucleic acid sequence in a locus of interest that is not located between two homology arms subjected to homologous recombination is detected via a digital PCR method.

Here, "between two homology arms" includes the two homology arms themselves. That is, the second probe does not hybridize to any of the two homology arms themselves.

Figure 2:
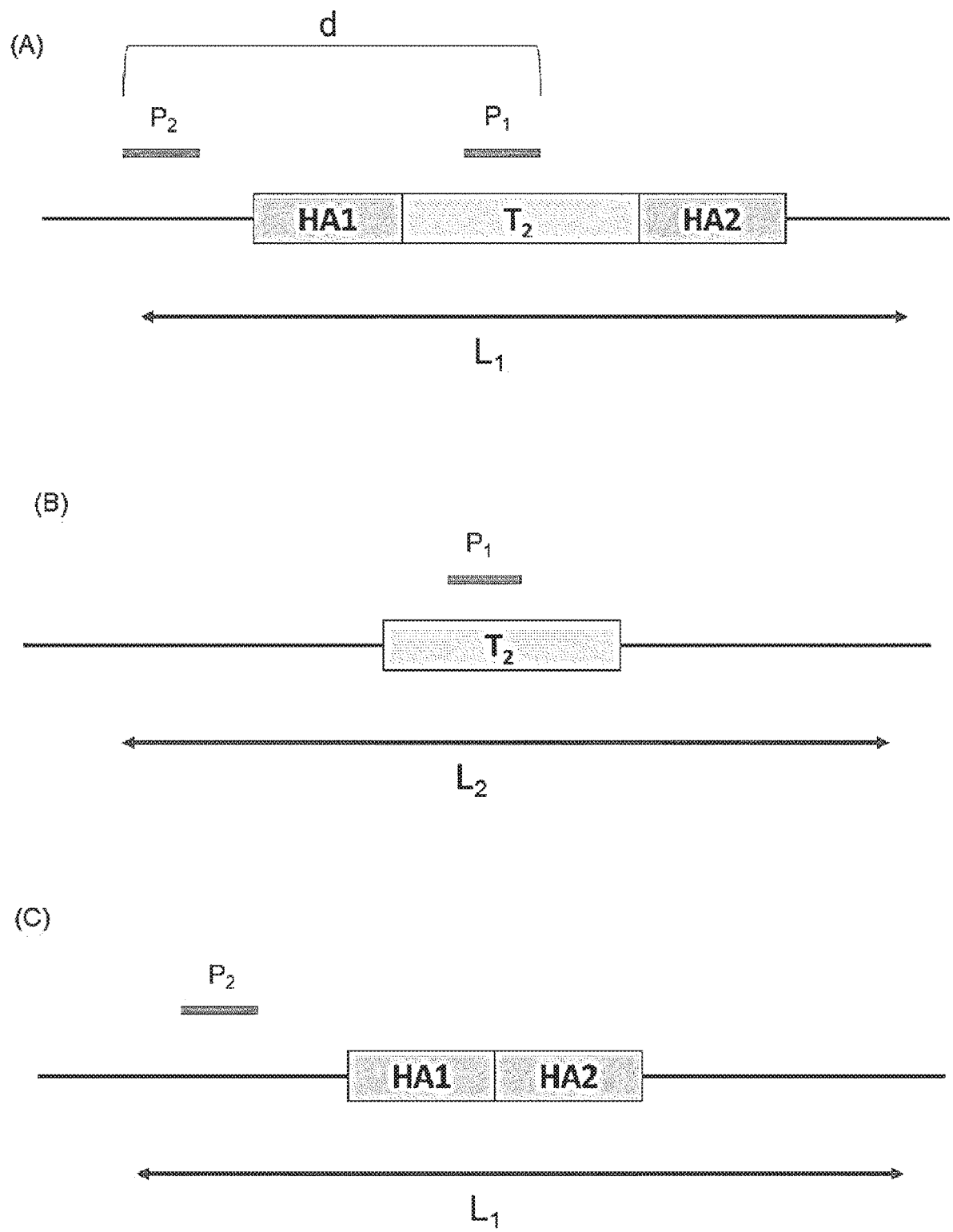
FIG. 2 describes a method of evaluating the knock-in efficiency, according to the present invention.

By referring to FIG. 2, a first probe nucleic acid and a second probe nucleic acid subjected to the digital PCR method will be described.

FIG. 2(A) shows an exogenous nucleic acid sequence $T_2$ present at a locus $L_1$ on the genomic DNA fragment.

A first probe nucleic acid $P_1$ (hereinafter, simply referred to as "Probe $P_1$") has a nucleotide sequence complementary to all or part of the exogenous nucleic acid sequence $T_2$ and specifically hybridizes to the exogenous nucleic acid sequence $T_2$.

A second probe nucleic acid $P_2$ (hereinafter, simply referred to as "Probe $P_2$") has a nucleotide sequence complementary to a nucleic acid sequence other than the exogenous nucleic acid sequence $T_2$ in the locus $L_1$ that is not located between two homology arms $HA_1$ and $HA_2$ subjected to homologous recombination, and specifically hybridizes to that nucleic acid sequence.

Here, "between the homology arm $HA_1$ and the homology arm $HA_2$" includes the homology arms $HA_1$ and $HA_2$ themselves. That is, Probe $P_2$ hybridize to neither homology arm $HA_1$ nor $HA_2$ itself.

Probe $P_1$ hybridizes to a nucleotide sequence within the exogenous nucleic acid sequence $T_2$ while Probe $P_2$ hybridizes to a nucleotide sequence outside of the exogenous nucleic acid sequence $T_2$, and therefore, in the locus $L_1$, a first region to which Probe $P_1$ can hybridize and a second region to which Probe $P_2$ can hybridize will be separated by a predetermined base length (distance d).

The distance d is about 0.1 kb to 100 kbs, preferably about 0.5 to 10 kbs, more preferably about 1 kb to 5 kbs, and further preferably about 1 kb to 2 kbs. The length of homology arms can be appropriately adjusted depending on the length of the exogenous nucleic acid sequence $T_2$, but is generally about 0.02 kb to 8 kbs, preferably about 0.04 kb to 3 kbs, and more preferably about 0.5 kb to 1.5 kbs.

Note that the second region to which Probe $P_2$ hybridizes is shown upstream of the homology arm $HA_1$ in the figure, but this region may be located downstream of the homology arm $HA_2$.

In a case where the insertion percentage (%) of the exogenous nucleic acid sequence $T_2$ into the locus $L_1$ in the test cell population is evaluated, hybridization of Probe $P_1$ and Probe $P_2$ to the genomic DNA fragment is quantified in this step. The quantification can be performed, in the digital PCR method, by calculating signal positive/negative in the microreaction regions after the reaction.

[Detection Step (3)]

In this step, the presence of the exogenous nucleic acid sequence $T_2$ is detected at the locus $L_1$ when Probe $P_1$ and Probe $P_2$ are hybridized to the genomic DNA fragment and double-positive is detected, and the absence of the exogenous nucleic acid sequence $T_2$ is detected at the locus $L_1$ based on the fact that only the hybridization of any one of Probe $P_1$ and Probe $P_2$ to the genomic DNA fragment is detected.

This will be described referring to FIG. 2.

In the first place, as shown in FIG. 2(A), when the exogenous nucleic acid sequence $T_2$ is present at the locus $L_1$ on the genomic DNA fragment, "double-positive" is detected in the digital PCR method, where both signals for Probe $P_1$ and Probe $P_2$ are positive. This indicates that the exogenous nucleic acid sequence $T_2$ is accurately inserted into the locus of interest $L_1$ via homologous recombination.

On the other hand, when a microreaction region in which the signal for Probe $P_1$ is positive and a microreaction region in which the signal for Probe $P_2$ is positive are present, but a microreaction region in which double-positive is detected is not present in the digital PCR method, as shown in FIG. 2(B), it is revealed that the exogenous nucleic acid sequence $T_2$ is present at a locus $L_2$ that is on some genomic DNA fragment and does not have the second region to which Probe $P_2$ hybridizes. This indicates that the exogenous nucleic acid sequence $T_2$ is inserted into the locus not of interest $L_2$ via a random integration.

In addition, when only the signal for Probe $P_2$ is positive and the signal for Probe $P_1$ is negative in the digital PCR method, as shown in FIG. 2(C), it is revealed that the exogenous nucleic acid sequence $T_2$ is not present at the locus $L_1$ that has the second region to which Probe $P_2$ hybridizes and is not present on any of genomic DNA fragments. This indicates that the exogenous nucleic acid sequence $T_2$ is not inserted onto the chromosome.

In a case where the insertion percentage (%) of the exogenous nucleic acid sequence $T_2$ into the locus $L_1$ in the test cell population is evaluated, the insertion percentage (%) is calculated based on the quantification results of hybridization of Probe $P_1$ and Probe $P_2$ to the genomic DNA fragment in the digital PCR step (2).

In particular, the insertion percentage (%) is calculated from a hybridization amount (double-positive: DP) of Probe $P_1$ and Probe $P_2$, and a hybridization amount (single positive 2: SP2) of Probe $P_2$ alone, according to the following formula.

Insertion percentage of exogenous nucleic acid sequence into locus of interest (%)=$DP$×100/($DP$+$SP2$)

Moreover, the random integration percentage (%) of the exogenous nucleic acid sequence $T_2$ into the chromosome can also be calculated according to the following formula.

Random integration percentage of exogenous nucleic acid sequence into chromosome (%)=$SP$1×100/($DP$+$SP2$)

Here, when a fragmentation of the chromosome between the first region to which Probe $P_1$ can hybridize and the second region to which Probe $P_2$ hybridizes in the locus $L_1$ occurs during the genomic DNA fragment preparation step (1), this leads to false negative of "single positive 1" and "single positive 2." When the fragmentation occurs, the calculated value of the insertion percentage (%) may be affected.

In order to eliminate the influence of the fragmentation, the method of evaluating the knock-in efficiency according to the present invention may further comprise the following steps.

(4) A step of using a probe pair (for example, Probes $P_3$ and $P_4$) that hybridizes to the chromosome with the distance of a base length corresponding to the base length between the first region and the second region and quantifying hybridization of the probe pair to the genomic DNA fragment via a digital PCR method, such that the following ratio in the genomic DNA fragment is calculated from a hybridization amount (dp) of both probes of the probe pair (Probes $P_3$ and $P_4$) and a hybridization amount (sp) of either one of the probe pair:

Fragmentation percentage (%)=$<sp>$×100/($dp$+$<sp>$)

(wherein, $<sp>$ denotes an average value of hybridization amounts of each probe of the probe pair).

(5) A step of correcting the insertion percentage (%) with the fragmentation percentage (%).

[Fragmentation Percentage (%) Calculation Step (4)]

Examples of methods of calculating the fragmentation percentage will be described below. In this step, a probe pair for estimating the rate of occurrence (%) of the fragmentation between the first region to which Probe $P_1$ can hybridize and the second region to which Probe $P_2$ hybridizes in the locus $L_1$ is provided. The probe pair (for example, Probe $P_3$ and Probe $P_4$) hybridizes to some region in the chromosome with the distance (that is, distance d) of a base length corresponding to the base length between the first region to which Probe $P_1$ can hybridize and the second region to which Probe $P_2$ hybridizes in the locus $L_1$. When a genomic DNA fragment in which not both probes of the probe pair hybridize and either one of the probes hybridizes is detected, this indicates that the fragmentation of the chromosome occurs between the hybridization regions of each probe (distance d), and its detection frequency (%) can be regarded as the rate of occurrence (%) of the fragmentation between the first region to which Probe $P_1$ can hybridize and the second region to which Probe $P_2$ hybridizes (distance d) in the locus $L_1$.

Therefore, the rate of occurrence (%) of the fragmentation in the locus $L_1$ can be calculated by quantifying hybridization of the probe pair to the genomic DNA fragment prepared in the genomic DNA fragment preparation step (1) via a digital PCR method, according to the following formula.

Fragmentation percentage (%)=$<sp>$×100/($dp$+$<sp>$)

(wherein, "dp" denotes a hybridization amount of both probes of the probe pair, and $<sp>$ denotes an average value of hybridization amounts of each probe of the probe pair. Note that the hybridization amounts of both probes theoretically match with each other, and thus, the hybridization amount of either one of the probes may be used for the calculation instead of the average value.)

This step may be performed for every genomic DNA fragment preparation step (1). Alternatively, this step may be omitted when the calculation of the fragmentation percentage (%) is once performed under certain extraction conditions and then the genomic DNA fragment preparation step (1) is performed under the same conditions, because the fragmentation percentage (%) can be regarded as the same level when the genomic DNA fragment preparation step (1) is performed under the same extraction conditions. In addition, this step may also be omitted when the fragmentation does not occur or when the rate of occurrence of the fragmentation is low enough to the extent of not affecting the calculated value of the insertion percentage (%), etc.

[Correction Step (5)]

In this step, the insertion percentage (%) is corrected with the fragmentation percentage (%).

In particular, in order to compensate an apparent decline in the numerical value by the fragmentation, the fragmentation percentage (%) is added to the value of insertion percentage (%) to obtain the actual insertion percentage (%).

4. Method of Evaluating Knockout Efficiency

The method of detecting the presence or absence of a nucleic acid sequence to be detected at a predetermined locus on the chromosome according to the present invention can also be applied to a method of evaluating the knockout efficiency.

The method of evaluating the knockout efficiency according to the present invention comprises the following steps.

(1) A step of preparing a genomic DNA fragment from a test cell or population thereof.
(2) A step of detecting, via a digital PCR method, the presence or absence of hybridization, to the genomic DNA fragment derived from a chromosome of the test cell, of
a first probe nucleic acid that hybridizes to all or part of an endogenous nucleic acid sequence contemplated to be deleted from, via genetic recombination, a locus of interest on the chromosome, and
a second probe nucleic acid that hybridizes to a nucleic acid sequence other than the endogenous nucleic acid sequence in the locus of interest that is not located between two homology arms subjected to the genetic recombination.
(3) A step of detecting the absence of the endogenous nucleic acid sequence at the locus of interest when double-positive is not obtained and hybridization of the second probe nucleic acid to the genomic DNA fragment is detected, and
of detecting the presence of the endogenous nucleic acid sequence at the locus of interest when the first probe nucleic acid and the second probe nucleic acid are hybridized to the genomic DNA fragment and double-positive is detected.

Here, the "endogenous nucleic acid sequence" may be any nucleic acid sequence, and can include all of nucleic acid sequences of a transcriptional region/non-transcriptional region, and nucleic acid sequences of a protein coding region/non-coding region. In addition, the base length of the endogenous nucleic acid sequence may be arbitrary.

[Genomic DNA Fragment Preparation Step (1)]

In this step, a genomic DNA fragment is prepared from a test cell contemplated to have an endogenous nucleic acid sequence deleted from, via genetic recombination, a locus of interest on a chromosome. Details of this step are as already described.

In a case where the deletion percentage (knockout efficiency) of an endogenous nucleic acid sequence in a test cell is evaluated, a genomic DNA fragment is prepared from a cell population of the test cell.

[Digital PCR Step (2)]

In this step, the presence or absence of hybridization, to a genomic DNA fragment, of a first probe nucleic acid that hybridizes to all or part of an endogenous nucleic acid sequence, and of a second probe nucleic acid that hybridizes to a nucleic acid sequence other than the endogenous nucleic acid sequence in a locus of interest that is not located between two homology arms subjected to genetic recombination is detected via a digital PCR method.

Here, "between two homology arms" includes the two homology arms themselves. That is, the second probe does not hybridize to any of the two homology arms themselves.

Figure 3:
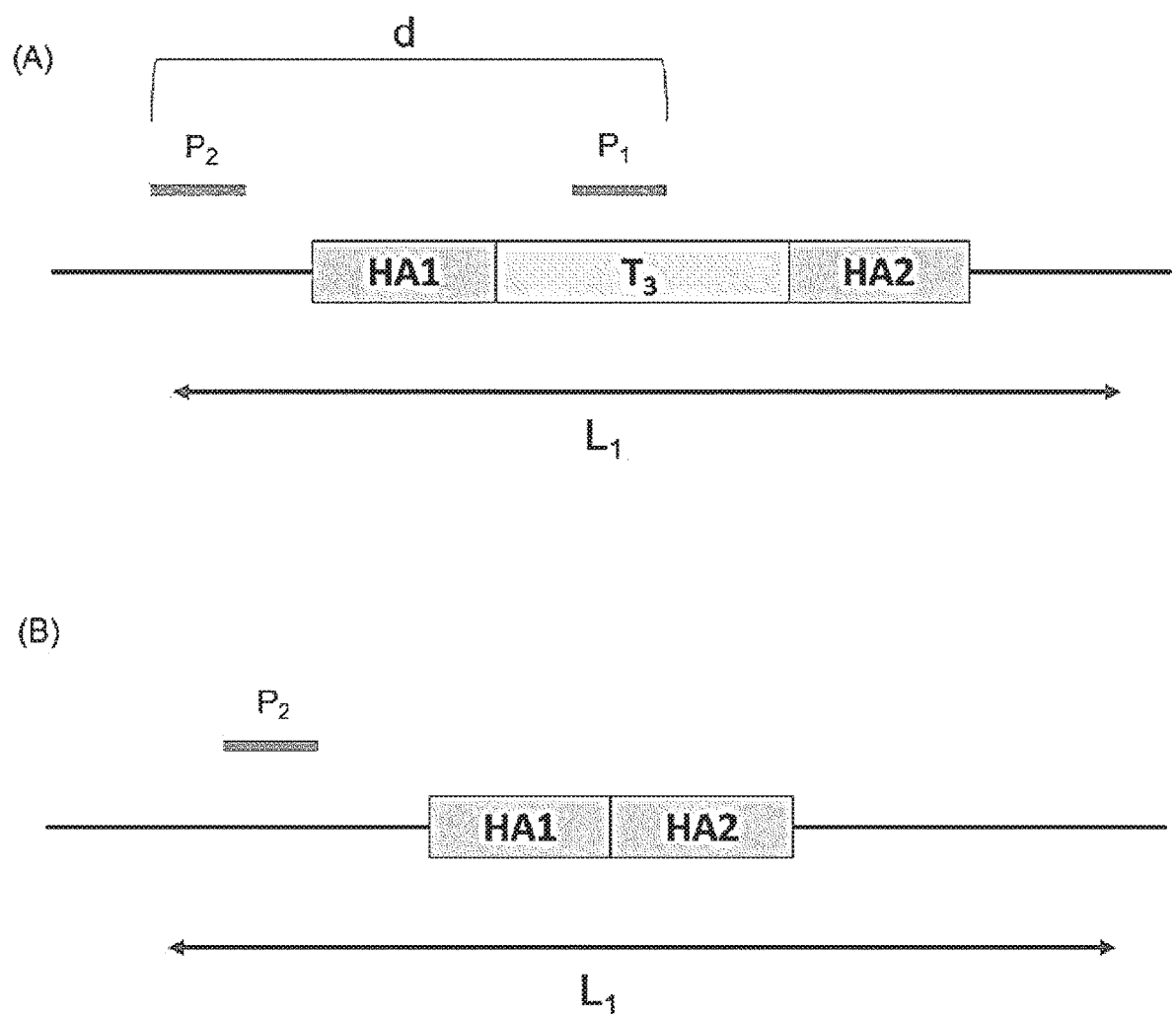
FIG. 3 describes a method of evaluating the knockout efficiency, according to the present invention.

By referring to FIG. 3, a first probe nucleic acid and a second probe nucleic acid subjected to the digital PCR method will be described.

FIG. 3(A) shows an endogenous nucleic acid sequence $T_3$ present at a locus $L_1$ on the genomic DNA fragment.

A first probe nucleic acid $P_1$ (hereinafter, simply referred to as "Probe $P_1$") has a nucleotide sequence complementary to all or part of the endogenous nucleic acid sequence $T_3$ and specifically hybridizes to the endogenous nucleic acid sequence $T_3$.

A second probe nucleic acid $P_2$ (hereinafter, simply referred to as "Probe $P_2$") has a nucleotide sequence complementary to a nucleic acid sequence other than the endogenous nucleic acid sequence $T_3$ in the locus $L_1$ that is not located between two homology arms $HA_1$ and $HA_2$ subjected to homologous recombination, and specifically hybridizes to that nucleic acid sequence.

Here, "between the homology arm $HA_1$ and the homology arm $HA_2$" includes the homology arms $HA_1$ and $HA_2$ themselves. That is, Probe $P_2$ hybridize to neither homology arm $HA_1$ nor $HA_2$ itself.

Probe $P_1$ hybridizes to a nucleotide sequence within the endogenous nucleic acid sequence $T_3$ while Probe $P_2$ hybridizes to a nucleotide sequence outside of the endogenous nucleic acid sequence $T_3$, and therefore, in the locus $L_1$, a first region to which Probe $P_1$ can hybridize and a second region to which Probe $P_2$ can hybridize will be separated by a predetermined base length (distance d).

The distance d is about 0.1 kb to 100 kbs, preferably about 0.5 to 10 kbs, more preferably about 1 kb to 5 kbs, and further preferably about 1 kb to 2 kbs. The length of homology arms can be appropriately adjusted depending on the length of the endogenous nucleic acid sequence $T_3$, but is generally about 0.02 kb to 8 kbs, preferably about 0.04 kb to 3 kbs, and more preferably about 0.5 kb to 1.5 kbs.

Note that the second region to which Probe $P_2$ hybridizes is shown upstream of the homology arm $HA_1$ in the figure, but this region may be located downstream of the homology arm $HA_2$.

In a case where the deletion percentage (%) of the endogenous nucleic acid sequence $T_3$ from the chromosome in the test cell population is evaluated, hybridization of Probe $P_1$ and Probe $P_2$ to the genomic DNA fragment is quantified in this step. The quantification can be performed, in the digital PCR method, by calculating signal positive/negative in the microreaction regions after the reaction.

[Detection Step (3)]

In this step, the absence of the endogenous nucleic acid sequence $T_3$ is detected at the locus $L_1$ based on the fact that only the hybridization of Probe $P_2$ to the genomic DNA fragment is detected, and the presence of the endogenous nucleic acid sequence $T_3$ is detected at the locus $L_1$ when Probe $P_1$ and Probe $P_2$ are hybridized to the genomic DNA fragment and double-positive is detected.

This will be described referring to FIG. 3.

In the first place, as shown in FIG. 3(A), when the endogenous nucleic acid sequence $T_3$ is present at the locus $L_1$ on the genomic DNA fragment, "double-positive" is detected in the digital PCR method, where both signals for Probe $P_1$ and Probe $P_2$ are positive. This indicates that the endogenous nucleic acid sequence $T_3$ is not deleted from the chromosome and remains at the locus of interest $L_1$.

On the other hand, when only the signal for Probe $P_2$ is positive and the signal for Probe $P_1$ is negative in the digital PCR method, as shown in FIG. 3(B), it is revealed that the endogenous nucleic acid sequence $T_3$ is deleted from the locus $L_1$ that has the second region to which Probe $P_2$ hybridizes and is not present on any of genomic DNA fragments. This indicates that the endogenous nucleic acid sequence $T_3$ is completely deleted from the chromosome.

In a case where the deletion percentage (%) of the endogenous nucleic acid sequence $T_3$ from the locus $L_1$ in the test cell population is evaluated, the deletion percentage (%) is calculated based on the quantification results of hybridization of Probe $P_1$ and Probe $P_2$ to the genomic DNA fragment in the digital PCR step (2).

In particular, the deletion percentage (%) is calculated from a hybridization amount (double-positive: DP) of Probe $P_1$ and Probe $P_2$, and a hybridization amount (single positive 2: SP2) of Probe $P_2$ alone, according to the following formula.

Deletion percentage of endogenous nucleic acid sequence (%)=100−$DP$×100/($DP+SP2$)

Here, when a fragmentation of the chromosome between the first region to which Probe $P_1$ can hybridize and the second region to which Probe $P_2$ hybridizes in the locus $L_1$ occurs during the genomic DNA fragment preparation step (1), this leads to false positive of "single positive 1" and "single positive 2." When such fragmentation occurs, the calculated value of the deletion percentage (%) may be affected.

In order to eliminate the influence of the fragmentation, the method of evaluating the knockout efficiency according to the present invention may further comprise the following steps.

(4) A step of using a probe pair (for example, Probe $P_3$ and Probe $P_4$) that hybridizes to the chromosome with the distance of a base length corresponding to the base length between the first region and the second region and quantifying hybridization of the probe pair to the genomic DNA fragment via a digital PCR method, such that the following ratio in the genomic DNA fragment is calculated from a hybridization amount (dp) of both probes of the probe pair (Probe $P_3$ and Probe $P_4$) and a hybridization amount (sp) of either one of the probe pair:

Fragmentation percentage (%)=$<sp>\times 100/(dp+<sp>)$ (wherein, $<sp>$ denotes an average value of hybridization amounts of each probe of the probe pair).

In addition, the fragmentation percentage for correcting the knockout efficiency can also be calculated as follows, using a hybridization amount of the probe pair (Probe $P_1$ and Probe $P_2$).

Fragmentation percentage (%)=$100\times SP1/(DP+SP2)$ (5) A step of correcting the deletion percentage (%) with the fragmentation percentage (%).

[Fragmentation Percentage (%) Calculation Step (4)]

Examples of methods of calculating the fragmentation percentage will be described below. In this step, a probe pair (for example, Probes $P_3$ and $P_4$) for estimating the rate of occurrence (%) of the fragmentation between the first region to which Probe $P_1$ can hybridize and the second region to which Probe $P_2$ hybridizes in the locus $L_1$ is provided. The probe pair hybridizes to some region in the chromosome with the distance (that is, distance d) of a base length corresponding to the base length between the first region to which Probe $P_1$ can hybridize and the second region to which Probe $P_2$ hybridizes in the locus $L_1$. When a genomic DNA fragment in which not both probes of the probe pair hybridize and either one of the probes hybridizes is detected, this indicates that the fragmentation of the chromosome occurs between the hybridization regions of each probe (distance d), and its detection frequency (%) can be regarded as the rate of occurrence (%) of the fragmentation between the first region to which Probe $P_1$ can hybridize and the second region to which Probe $P_2$ hybridizes (distance d) in the locus $L_1$.

Therefore, the rate of occurrence (%) of the fragmentation in the locus $L_1$ can be calculated by quantifying hybridization of the probe pair to the genomic DNA fragment prepared in the genomic DNA fragment preparation step (1) via a digital PCR method, according to the following formula.

Fragmentation percentage (%)=$<sp>\times 100/(dp+<sp>)$ (wherein, "dp" denotes a hybridization amount of both probes of the probe pair, and $<sp>$ denotes an average value of hybridization amounts of each probe of the probe pair. Note that the hybridization amounts of both probes theoretically match with each other, and thus, the hybridization amount of either one of the probes may be used for the calculation instead of the average value.)

This step may be performed for every genomic DNA fragment preparation step (1). Alternatively, this step may be omitted when the calculation of the fragmentation percentage (%) is once performed under certain extraction conditions and then the genomic DNA fragment preparation step (1) is performed under the same conditions, because the fragmentation percentage (%) can be regarded as the same level when the genomic DNA fragment preparation step (1) is performed under the same extraction conditions. In addition, this step may also be omitted when the fragmentation does not occur or when the rate of occurrence of the fragmentation is low enough to the extent of not affecting the calculated value of the deletion percentage (%), etc.

[Correction Step (5)]

In this step, the deletion percentage (%) is corrected with the fragmentation percentage (%).

In particular, in order to compensate an apparent increase in the numerical value by the fragmentation, the fragmentation percentage (%) is subtracted from the value of deletion percentage (%) to obtain the actual deletion percentage (%).

A. Method of Evaluating Knockout Efficiency

With a quantitative PCR or a digital PCR on the genome of a cell subjected to modification of a target site in the genome as a template, the ratio of mutation in the sequence that occurs in a DSB-dependent manner can be measured. In this case, a probe designed for a sequence on the genome to which DSB occurs can detect the wild-type sequence, but it does not detect a mutated sequence with base insertion or deletion resulting from repair by NHEJ that takes place after DSB. Accordingly, the decrement of the signal compared to the genome of the wild-type cell can be quantified as the ratio of mutation, and this ratio of mutation can be regarded as the knockout efficiency. Conveniently, the ratio of variation can also be confirmed based on the cleavage ratio using T7 Endonuclease I or Cel-I enzyme. For more specific steps, based on the genome of a cell subjected to modification of a target site in the genome, a region to which DSB occurs is PCR-amplified such that the full length becomes about 100 to 700 bps. The resultant fragments are mixed with fragments that have been amplified similarly based on the wild-type genome, and heated at about 95° C. for around 1 minute and then naturally cooled to prepare heteroduplexes of amplification products of the variant and the wild type. After the treatment with T7 Endonuclease I or Cel-I enzyme that cleaves heteroduplexes, the KO efficiency can be obtained by evaluating, with electrophoresis, the ratio of heteroduplexes subjected to the cleavage. The method of calculating the mutation introduction efficiency is performed according to the calculation formula below. The mutation introduction efficiency can be obtained by the following formula:

$F\text{cut}=(b+c)/(a+b+c)$ indel (%)=$100\times(1-\text{sqrt}((1-F\text{cut})))$ wherein the area of a peak from the uncleaved band is a, and peaks from the cleaved band are b and c. This can be used as the KO efficiency.

B. Method of Evaluating Knock-in Efficiency Via HR

A method of evaluating the knock-in efficiency via HR according to the present invention is characterized by including the following steps.

(A) A step of performing digital PCR on the genome of a cell subjected to HR as a template using a probe designed for the outside of a sequence that is substantially the same as homology arms of the chromosome and a probe designed for the inside of a targeting cassette.

The digital PCR is an approach of quantitatively measuring nucleic acids included in a sample by introducing a sample including nucleic acids into numerous microreaction regions, performing PCR, and detecting the presence or absence of production of amplification products in each reaction region. In the digital PCR, the sample is diluted for the purpose of introducing only one molecule of nucleic acid or no nucleic acid into each reaction region. Accordingly, by detecting the presence or absence of production of amplification products in each reaction region after the reaction of PCR, the presence or absence of the nucleic acid at the initial stage after introduction of the sample in each reaction region can be determined. The absolute amount of nucleic acids in the sample can be determined by digitalizing the presence and absence of the nucleic acid at the initial stage after introduction of the sample in each reaction region with a numerical value of 1 (with nucleic acid) or 0 (without nucleic acid), and by analyzing numerical values acquired at numerous reaction regions. The basic methodology for the digital PCR is described in, for example, Sykes et al., Biotechniques 13 (3): 444-449, 1992.

Figure 4:
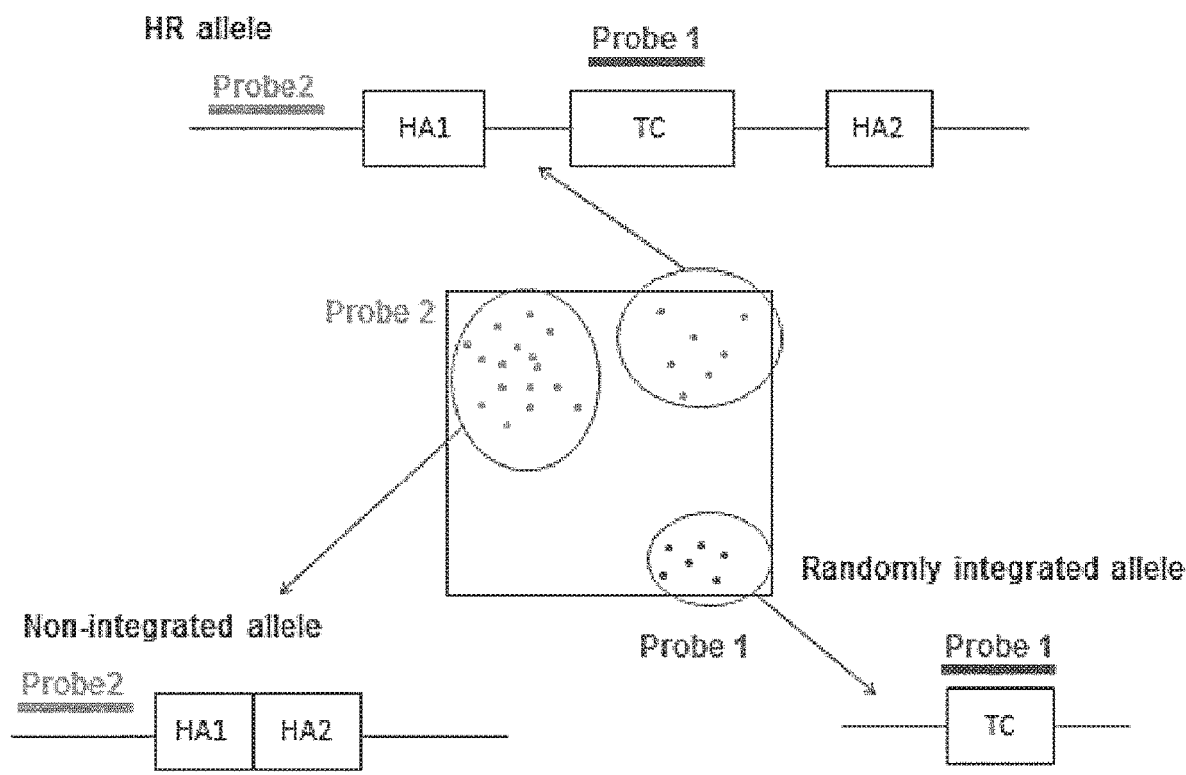
FIG. 4 describes a method of evaluating the knock-in efficiency via homologous recombination (HR), according to the present invention.

The method according to the present invention enables evaluation of the knock-in efficiency via HR, and is characterized by including the step (A) described above. Hereinafter, this will be specifically described referring to FIG. 4.

The knock-in via HR is typically performed using a targeting vector comprising two homology arms (HA1 and HA2) and a targeting cassette (TC) that includes an exogenous nucleic acid sequence. In this case, for an allele (see "HR allele" in the figure) into which a targeting cassette is inserted via HR, a probe 2 that hybridizes to the outside of HA1 (upstream in the figure) and a probe 1 that hybridizes to the inside of TC can be designed. Note that the probe 2 is just required to be designed for the outside of the homology arms, and may be designed for the downstream of HA2.

For an allele ("Non-integrated allele" in the figure) into which a targeting cassette is not inserted via HR, only the probe 2 that is designed for the outside of HA1 (upstream in the figure) can hybridize. In addition, for an allele ("Randomly integrated allele" in the figure) in which an unexpected insertion of the targeting cassette occurs via a random integration, only the probe 1 that is designed for the inside of TC can hybridize.

Accordingly, by detecting, in the digital PCR, the presence or absence of hybridization of the probe 1 and the probe 2 in each detection field, the abundance of each allele out of "HR allele", "Non-integrated allele" and "Randomly integrated allele" can be measured. In particular, a detection field in which the probe 1 and the probe 2 are double-positive indicates the presence of "HR allele", a detection field in which only the probe 2 is single positive indicates the presence of "Non-integrated allele", and a detection field in which only the probe 1 is single positive indicates the presence of "Randomly integrated allele."

According to the ratio of the abundance of "HR allele" to the abundance of "Non-integrated allele", the "insertion percentage of exogenous nucleic acid sequence" at a target site can be evaluated. In addition, according to the ratio of the abundance of "HR allele" to the abundance of "Randomly integrated allele", the "insertion percentage into target site" of an exogenous nucleic acid sequence can be evaluated.

Quantitative detection of hybridization of the probe 1 and the probe 2 to the genome can be performed based on conventionally known digital PCR. For example, as the probe 1 and the probe 2, a combination of fluorescence labeled TaqMan Probe and TaqMan Primer is available from a commercial entrustment service (Thermo Fisher Scientific). In addition, as a kit for real-time PCR, QuantStudio 3D Digital PCR Master Mix is available, and as an analysis apparatus, a Droplet digital PCR apparatus, QuantStudio 3D and a QuantStudio 3D AnalysisSuite software (all from Thermo Fisher Scientific) are available.

In accordance with the method of modifying a target site in the genome according to the present invention, a technology for modifying a target site in the genome of a cell with a high specificity and efficiency, using a template nucleic acid of an RNA-guided nuclease, and a template nucleic acid of a gRNA or a gRNA can be provided. From another point of view, the problem for the present invention is to be able to efficiently select cells in which a desired modification is produced at the target site in the genome. When cells in which the genome of interest has been modified can be obtained at a high efficiency, it is possible to enhance time efficiency and economical efficiency for drug screening using those cells of interest, induction to differentiated cells from those cells of interest, etc. More particularly, for example, examples of problems include that, when modification of a target site in the genome of a cell is performed for the purpose of subjecting the cell to drug screening, conventional methods allow a high abundance ratio of cells through random integrations such that it is not possible to perform drug screening with appropriate cells and to obtain reliable screening results. Therefore, another operation for modifying the target site in the genome is required, and the time efficiency and economical efficiency may be reduced. In accordance with the method of modifying a target site in the genome according to the present invention, cells of interest can be obtained at a high efficiency, thereby being able to avoid the problems as described above and to contribute to acquisition of reliable data or improvement in time efficiency and economical efficiency.

EXAMPLES

Example 1: Improvement in Knock-in Efficiency Via Cotransfection of Selection Plasmid Insertion of an artificial nucleic acid sequence (exogenous nucleic acid sequence) was performed to a target site of Adenomatous polyposis coli (APC) gene in the genome of a cell. For a nuclease template nucleic acid, a gRNA template nucleic acid, a targeting template nucleic acid and a selection template nucleic acid, a plasmid vector expressing Cas9 of *Streptococcus pyogenes* (nuclease vector, Cas9), a plasmid vector expressing a gRNA (gRNA vector, APCAS56), a plasmid vector comprising an artificial nucleic acid sequence (targeting vector, APCshort #2) and a plasmid vector expressing a puromycin resistance gene (selection vector, pEBmultipuro) were used, respectively. The mixture of these plasmid vectors was transfected to a colon carcinoma cell line, HCT-116 at a condition of 500,000 cells/10 µl via an electroporation method. For the transfection, reagents and electroporation parameters for HCT-116 of Neon (Invitrogen) were used. APCshort #2 has a nucleic acid sequence in which part of exon 3 of APC gene (SEQ ID NO: 1) has been deleted. The nucleotide sequence of exon 3 of APC gene and the gRNA recognition sequence (SEQ ID NO: 2) are shown in FIG. 5.

The transfection was performed with varying ratios (molar ratios) of the puromycin resistance gene expressing plasmid to the total amount of the entire plasmids, as shown in "Table 1."

TABLE 1

|  |  | Sample 1 | Sample 2 | Sample 3 | Sample 4 | Sample 5 |
|---|---|---|---|---|---|---|
| (a) Nuclease vector | spCas9 (mol)(A) | 40.6 | 40.6 | 40.6 | 40.6 | 40.6 |
| (b) gRNA vector | APCAS56(mol)(B) | 61.5 | 61.5 | 61.5 | 61.5 | 61.5 |
| (c) Selection vector | pEBmultipuro(mol) (C) | 1.08 | 2.15 | 4.30 | 8.61 | 17.21 |
| (d) Targeting vector | APCshort#2(mol)(D) | 77.7 | 77.7 | 77.7 | 77.7 | 77.7 |
| Molar ratio of selection vector | C/A + B + C + D | 0.0059 | 0.0118 | 0.0234 | 0.0457 | 0.0873 |
| Factor value | C × 4/A + B + C + D | 0.0238 | 0.0473 | 0.0934 | 0.1827 | 0.3494 |

From 24 hours after the transfection, cell culture was performed for 10 days under the presence of puromycin at 1 μg/ml, and puromycin resistance gene expressing cells were selected. The genomic DNA was extracted from the selected cells to perform the following PCR analysis.

To obtain information of the genome while avoiding the influence of the remaining targeting template nucleic acid, a forward primer (SEQ ID NO: 3: CTTGCACAGA-GACTCCCCATAATCACC) was designed upstream of the homology sequence of the targeting template nucleic acid, and a reverse primer (SEQ ID NO: 4: ACTTTCTCTGCTTCCATTTACAAACCCTCTTC) was designed downstream of the deletion region of the template plasmid. With this primer pair, PCR was performed on the genomic DNA collected from transfection groups of the samples 1 to 5 as a template. An amplification product of wild-type APC gene is 1256 bps (SEQ ID NO: 5) and an amplification product of APC gene into which an artificial nucleic acid sequence is inserted is 1191 bps (SEQ ID NO: 6). The nucleotide sequence of each amplification product is shown in FIG. 6.

In order to more clearly detect decrease in the length of the amplification product caused by the insertion of the artificial nucleic acid sequence, after performing digestion with a restriction enzyme (MfeI), microchip electrophoresis was performed. A digestion fragment of 206 bps was detected from the amplification product of wild-type APC gene, and a digestion fragment of 147 bps was detected from the amplification product of APC gene into which the artificial nucleic acid sequence is inserted.

Figure 7:
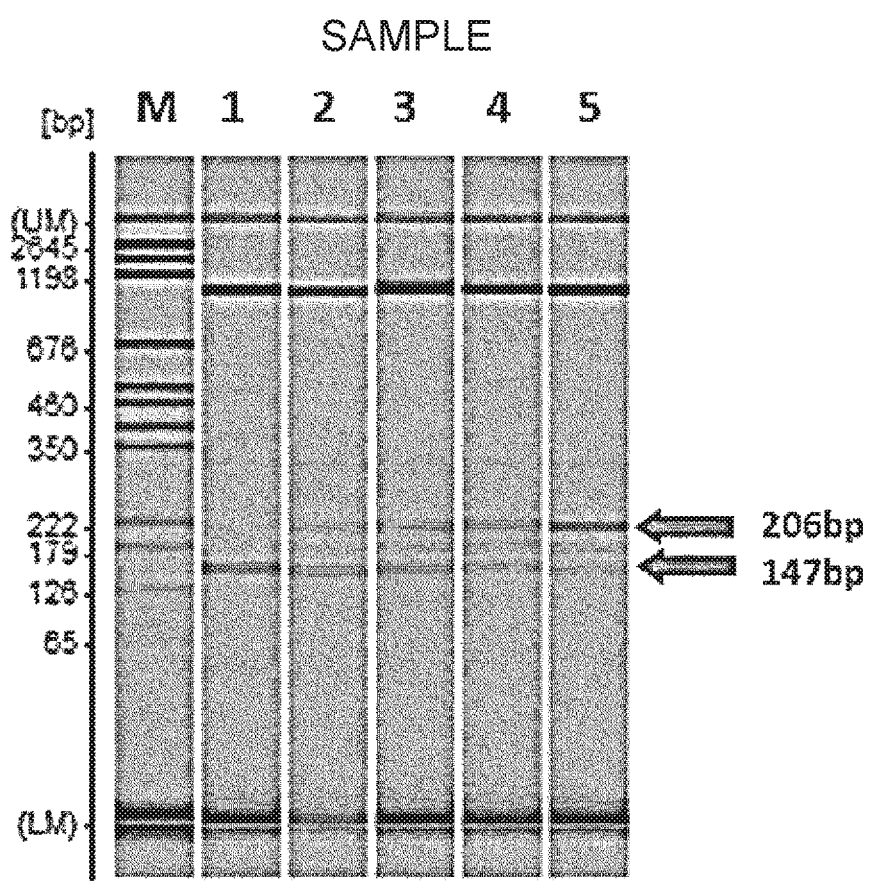
FIG. 7 shows electrophoretic patterns of fragments resulting from digestion with a restriction enzyme of an amplification product of wild-type APC gene and of an amplification product of APC gene into which an artificial nucleic acid (exogenous nucleic acid sequence) is inserted (Example 1).

Results of the electrophoresis are shown in FIG. 7. It has been observed that, as the rate of dilution of the selection vector (pEBmultipuro) increases, the amplification product of wild-type APC gene decreases and the amplification product of APC gene into which the artificial nucleic acid sequence is inserted increases. That is, it is obvious that, as the rate of dilution of the selection vector increases, the insertion efficiency of the artificial nucleic acid sequence increases.

Figure 8:
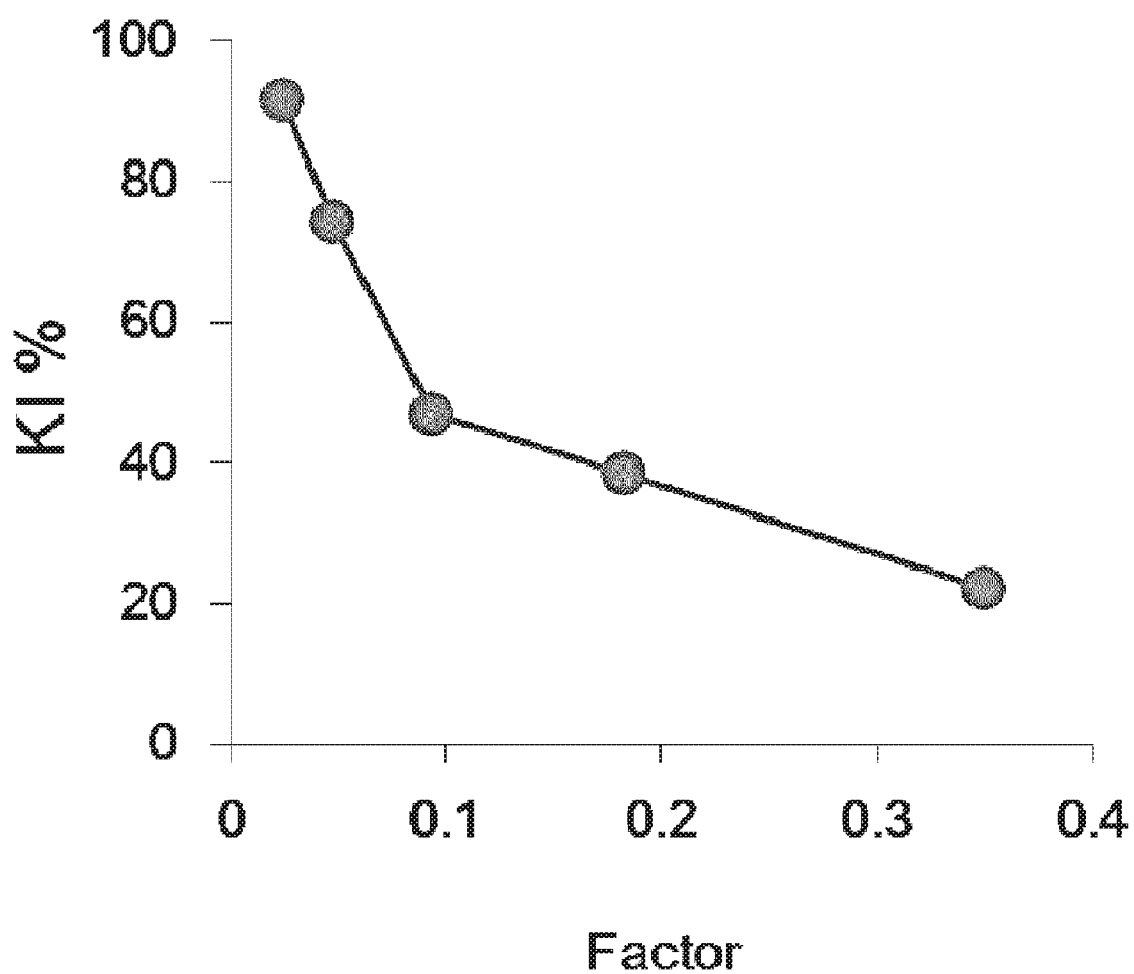
FIG. 8 shows a result obtained by calculating, based on the amount (X) of an amplification product of wild-type APC gene and the amount (Y) of an amplification product of APC gene into which an artificial nucleic acid (exogenous nucleic acid sequence) is inserted, the knock-in efficiency (=100×Y/(X+Y)) and plotting it relative to the Factor value (Example 1). The horizontal axis represents the Factor value and the vertical axis represents the knock-in efficiency (%).
Figure 9:
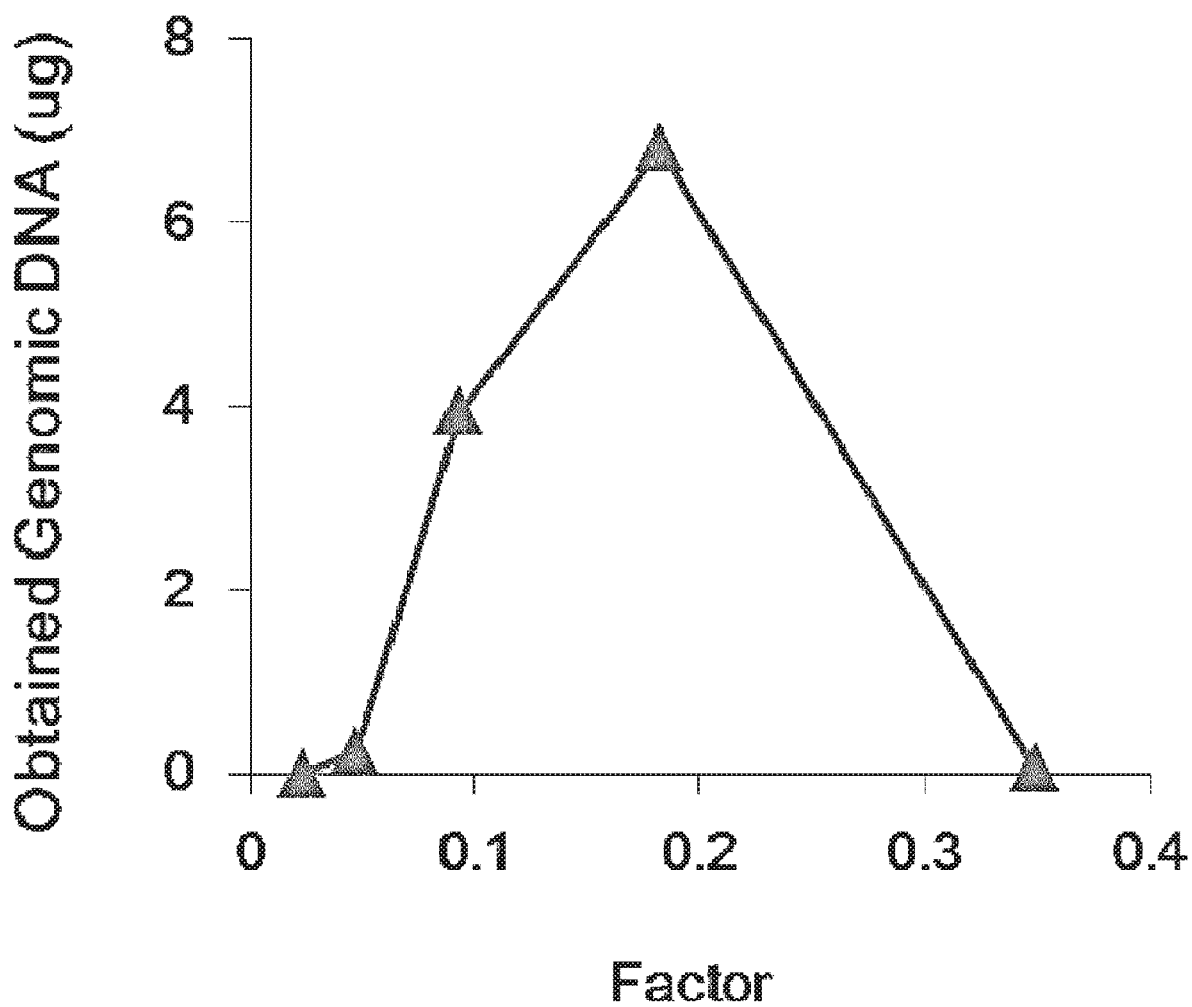
FIG. 9 shows a result obtained by plotting the mass of the genomic DNA collected relative to the Factor value (Example 1). The horizontal axis represents the Factor value and the vertical axis represents the mass of the genomic DNA (m).

FIG. 8 shows a result of the knock-in efficiency (=100× Y/(X+Y)) calculated by quantifying the amount (X) of the amplification product of wild-type APC gene and the amount (Y) of the amplification product of APC gene into which the artificial nucleic acid sequence is inserted through the quantification of the band concentration. In the figure, the horizontal axis represents the rate of dilution of the selection vector (pEBmultipuro) in transfection groups of the samples 1 to 5, and the vertical axis represents the knock-in efficiency (%). In addition, the total amount of the genomic DNA collected upon this is shown in FIG. 9. In the figure, the horizontal axis represents the rate of dilution of the selection vector (pEBmultipuro) in transfection groups of the samples 1 to 5, and the vertical axis represents the amount of the genomic DNA that was not able to be collected. In samples 1 to 4, especially in samples 1 and 2, it can be said that more efficient modification of the target site in the genome was performed from the viewpoint of the knock-in efficiency and the amount of the genomic DNA.

Example 2: Improvement in Knock-in Efficiency Via Cotransfection of Selection Plasmid (Artificial Nucleic Acid Sequence Changed)

Insertion of an artificial nucleic acid sequence (exogenous nucleic acid sequence) was performed in the same manner as Example 1 expect that TNNI1 gene in the genome of a cell was used as a target site.

For the targeting template nucleic acid (targeting oligo) comprising an artificial nucleic acid sequence, TNNIOligo having a nucleic acid sequence in which a nucleic acid sequence of 20 bps has been inserted into exon 7 of TNNI1 gene was used, and for the plasmid vector expressing a gRNA (gRNA vector), TNNI207 was used. The gRNA recognition sequence in the nucleotide sequence of exon 7 of TNNI1 gene is shown in SEQ ID NO: 7.

The transfection was performed with varying ratios (molar ratios) of the puromycin resistance gene expressing plasmid to the total amount of the entire introduction nucleic acids, cell culture was performed under the presence of puromycin, and puromycin resistance gene expressing cells were selected. The genomic DNA was extracted from the selected cells to perform the following PCR analysis.

A forward primer (SEQ ID NO: 8: GAACGTGGAGGC-CATGTCT) was designed upstream of the homology sequence of the targeting template nucleic acid, and a reverse primer (SEQ ID NO: 9: TAAGTA-CAACCCGCCTGCC) was designed downstream of the deletion region of the template plasmid. PCR was performed on the genomic DNA collected as a template using this primer pair. An amplification product of wild-type TNNI1 gene is 166 bps and an amplification product of TNNI1 gene into which an artificial nucleic acid sequence is inserted is 186 bps.

Figure 10:
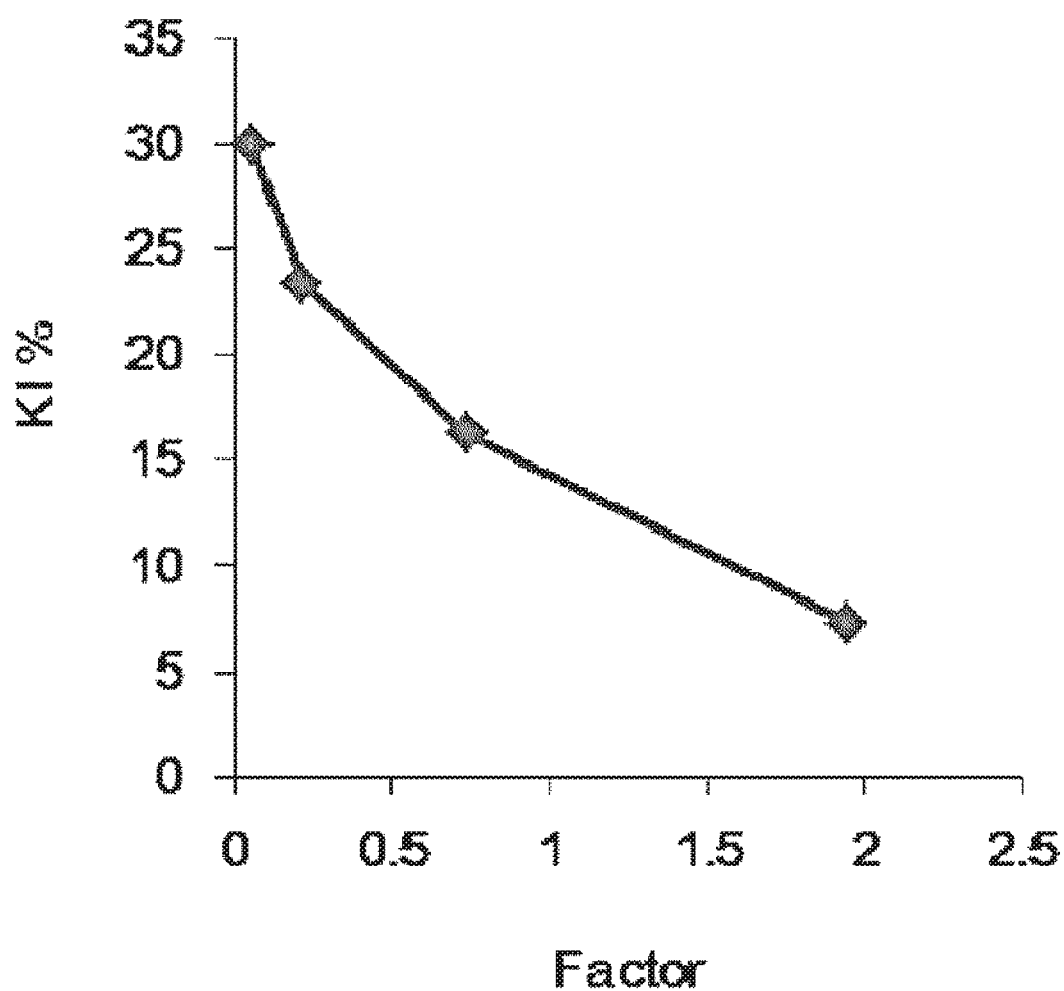
FIG. 10 shows a result obtained by calculating, based on the amount (X) of an amplification product of wild-type TNNI1 gene and the amount (Y) of an amplification product of TNNI1 gene into which an artificial nucleic acid sequence is inserted, the knock-in efficiency (=100×Y/(X+Y)) and plotting it relative to the Factor value (Example 2). The horizontal axis represents the Factor value and the vertical axis represents the knock-in efficiency (%).
Figure 11:
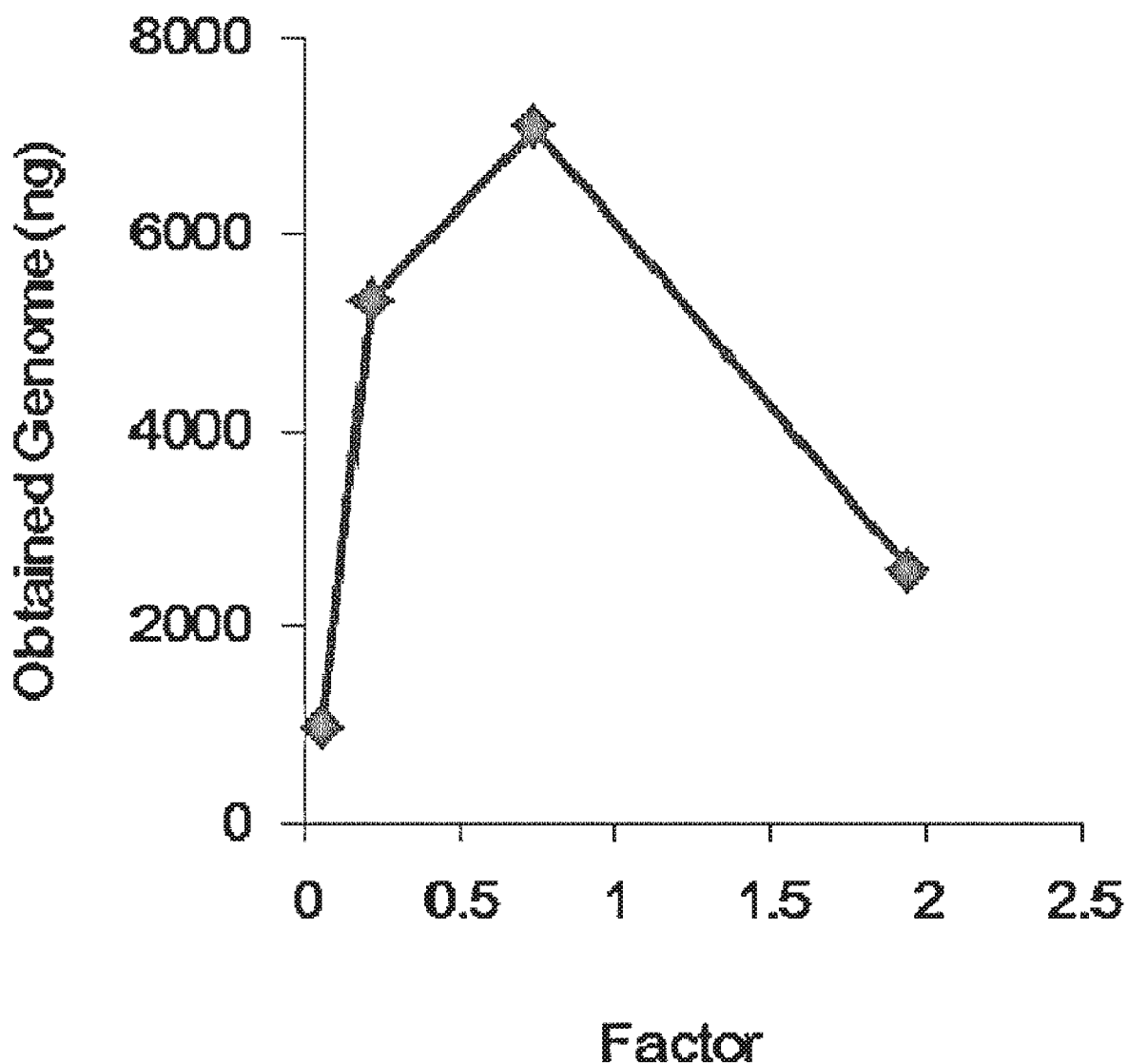
FIG. 11 shows a result obtained by plotting the mass of the genomic DNA collected relative to the Factor value (Example 2). The horizontal axis represents the Factor value and the vertical axis represents the mass of the genomic DNA (ng).

FIG. 10 shows a result of the knock-in efficiency (=100× Y/(X+Y)) calculated by quantifying the amount (X) of the amplification product of wild-type TNNI1 gene and the amount (Y) of the amplification product of TNNI1 gene into which the artificial nucleic acid sequence is inserted through the quantification of the band concentration. In the figure, the horizontal axis represents the rate of dilution of the selection vector (pEBmultipuro), and the vertical axis represents the knock-in efficiency (%). In addition, the total amount of the genomic DNA collected upon this is shown in FIG. 11. In the figure, the horizontal axis represents the rate of dilution of the selection vector (pEBmultipuro), and the vertical axis represents the amount of the genomic DNA that was not able to be collected. When the Factor value gets lower, the higher knock-in efficiency is obtained. When the Factor value was within a range of 0.056 to 0.21, more efficient modification of the target site in the genome was achieved from the viewpoint of the knock-in efficiency and the amount of the genomic DNA.

Example 3: Improvement in Knock-in Efficiency Via Cotransfection of Selection Plasmid (Cell and Artificial Nucleic Acid Sequence Changed)

Insertion of an artificial nucleic acid sequence (exogenous nucleic acid sequence) was performed in the same manner as Example 2 expect that a cell was changed to a cervical carcinoma cell line, HeLa. That is, from Example 1, a cell was changed to a cervical carcinoma cell line, HeLa, and a target site in the genome was changed to TNNI1 gene.

The transfection was performed with varying ratios (molar ratios) of the puromycin resistance gene expressing plasmid to the total amount of the entire introduction nucleic acids, cell culture was performed under the presence of puromycin, and puromycin resistance gene expressing cells were selected. The genomic DNA was extracted from the selected cells to perform the following PCR analysis.

Figure 12:
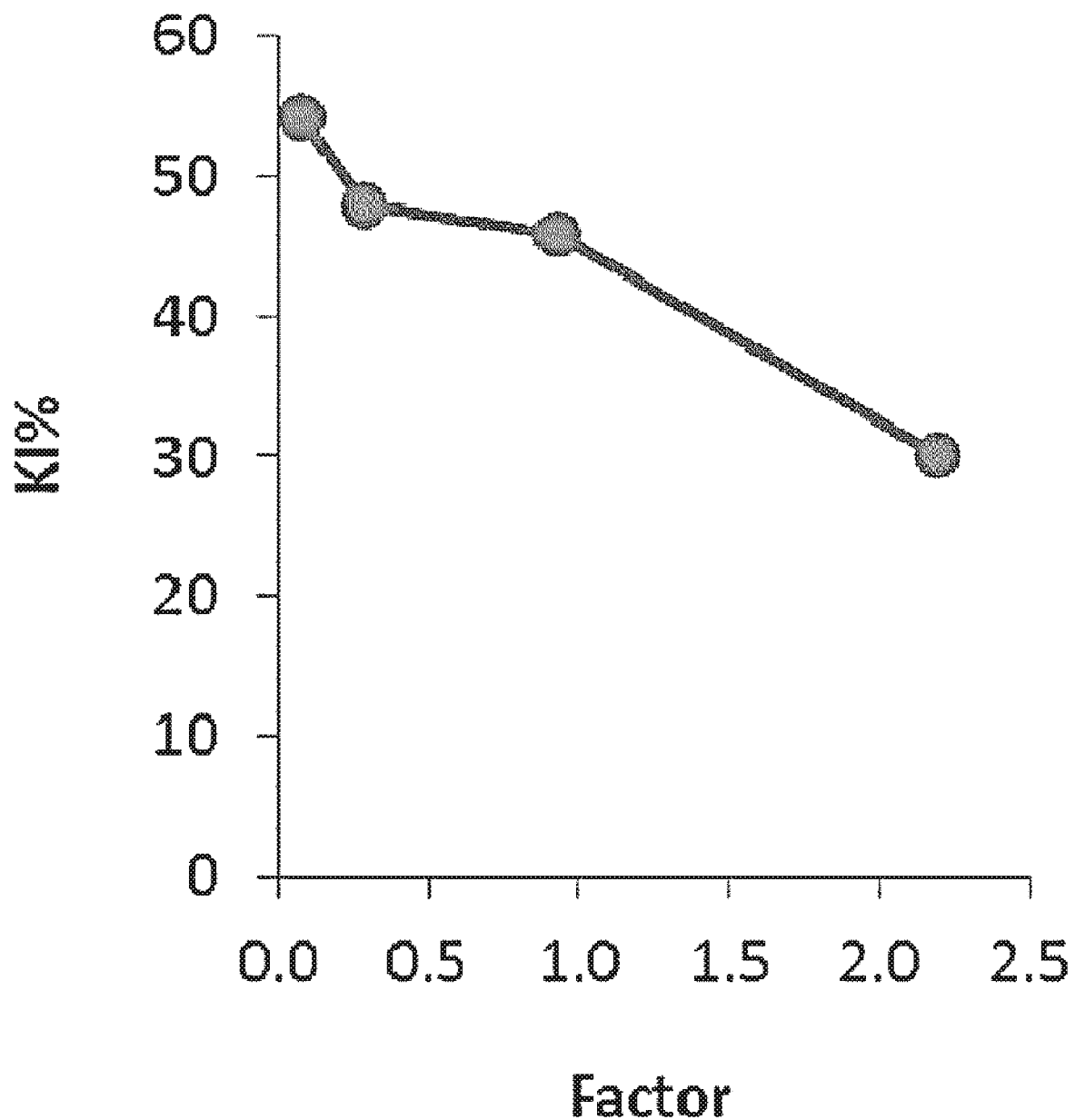
FIG. 12 shows a result obtained by calculating, based on the amount (X) of an amplification product of wild-type TNNI1 gene and the amount (Y) of an amplification product of TNNI1 gene into which an artificial nucleic acid sequence is inserted, the knock-in efficiency (=100×Y/(X+Y)) and plotting it relative to the Factor value (Example 3). The horizontal axis represents the Factor value and the vertical axis represents the knock-in efficiency (%).
Figure 13:
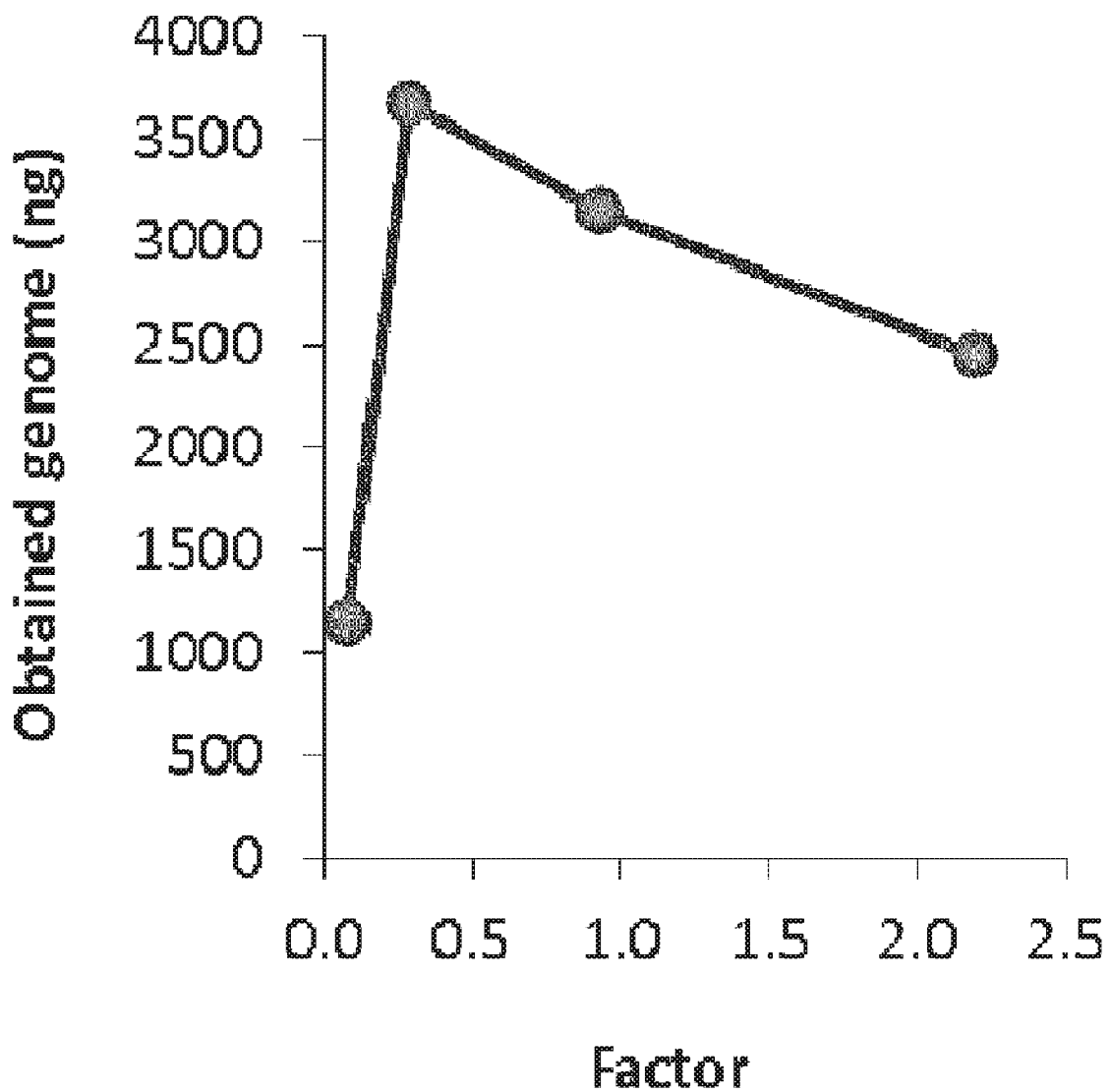
FIG. 13 shows a result obtained by plotting the mass of the genomic DNA collected relative to the Factor value (Example 3). The horizontal axis represents the Factor value and the vertical axis represents the mass of the genomic DNA (ng).

FIG. 12 shows a result of the knock-in efficiency (=100× Y/(X+Y)) calculated by quantifying the amount (X) of the amplification product of wild-type TNNI1 gene and the amount (Y) of the amplification product of TNNI1 gene into which the artificial nucleic acid sequence is inserted through the quantification of the band concentration. In the figure, the horizontal axis represents the rate of dilution of the selection vector (pEBmultipuro), and the vertical axis represents the knock-in efficiency (%). In addition, the total amount of the genomic DNA collected upon this is shown in FIG. 13. In the figure, the horizontal axis represents the rate of dilution of the selection vector (pEBmultipuro), and the vertical axis represents the amount of the genomic DNA that was not able to be collected. When the Factor value gets lower, the higher knock-in efficiency is obtained. When the Factor value was within a range of 0.074 to 0.28, more efficient modification of the target site in the genome was achieved from the viewpoint of the knock-in efficiency and the amount of the genomic DNA.

For various cells other than HeLa and HCT-116, insertion experiments of an artificial nucleic acid sequence (exogenous nucleic acid sequence) were also performed in the same manner, and effects of the ratio (molar ratio) of the selection vector to the total amount of the entire introduction nucleic acids exerting on the knock-in efficiency were verified. As a result, for example, in iPS cells (201B7 line), the knock-in efficiency of 100% was ascertained when the Factor value was 0.1748.

Example 4: Improvement in Knock-in Efficiency Via Cotransfection of Selection Plasmid (RNA-Guided Nuclease, Cell and Artificial Nucleic Acid Sequence Changed)

Insertion of an artificial nucleic acid sequence (exogenous nucleic acid sequence) was performed in the same manner as Example 1 expect that a plasmid vector expressing Cpf1 of *Acidaminococcus* sp. was used for the nuclease vector, a cell was changed to a cervical carcinoma cell line, HeLa, and a target site in the genome was changed to IPTKB gene.

For the targeting template nucleic acid (targeting oligo) comprising an artificial nucleic acid sequence, IPTKB12delID140 having a nucleic acid sequence in which 12 bps has been deleted from exon 8 of IPTKB gene was used, and for the plasmid vector expressing a gRNA (gRNA vector), pENTER_SSA_Cpf1 was used. The nucleotide sequence of exon 8 of IPTKB gene and the gRNA recognition sequence (SEQ ID NO: 10) are shown in FIG. 14.

The transfection was performed with varying ratios (molar ratios) of the puromycin resistance gene expressing plasmid to the total amount of the entire introduction nucleic acids, cell culture was performed under the presence of puromycin, and puromycin resistance gene expressing cells were selected. The genomic DNA was extracted from the selected cells to perform the following PCR analysis.

A forward primer (SEQ ID NO: 11: ATTGAGCCCCGAGAGGTAGCCATCCT) was designed upstream of the homology sequence of the targeting template nucleic acid, and a reverse primer (SEQ ID NO: 12: GGGCTTCAGCTCACCCTTCAC) was designed downstream of the deletion region of the template plasmid. PCR was performed on the genomic DNA collected as a template using this primer pair. An amplification product of wild-type IPTKB gene is 206 bps and an amplification product of IPTKB gene into which an artificial nucleic acid sequence is inserted is 186 bps.

Figure 15:
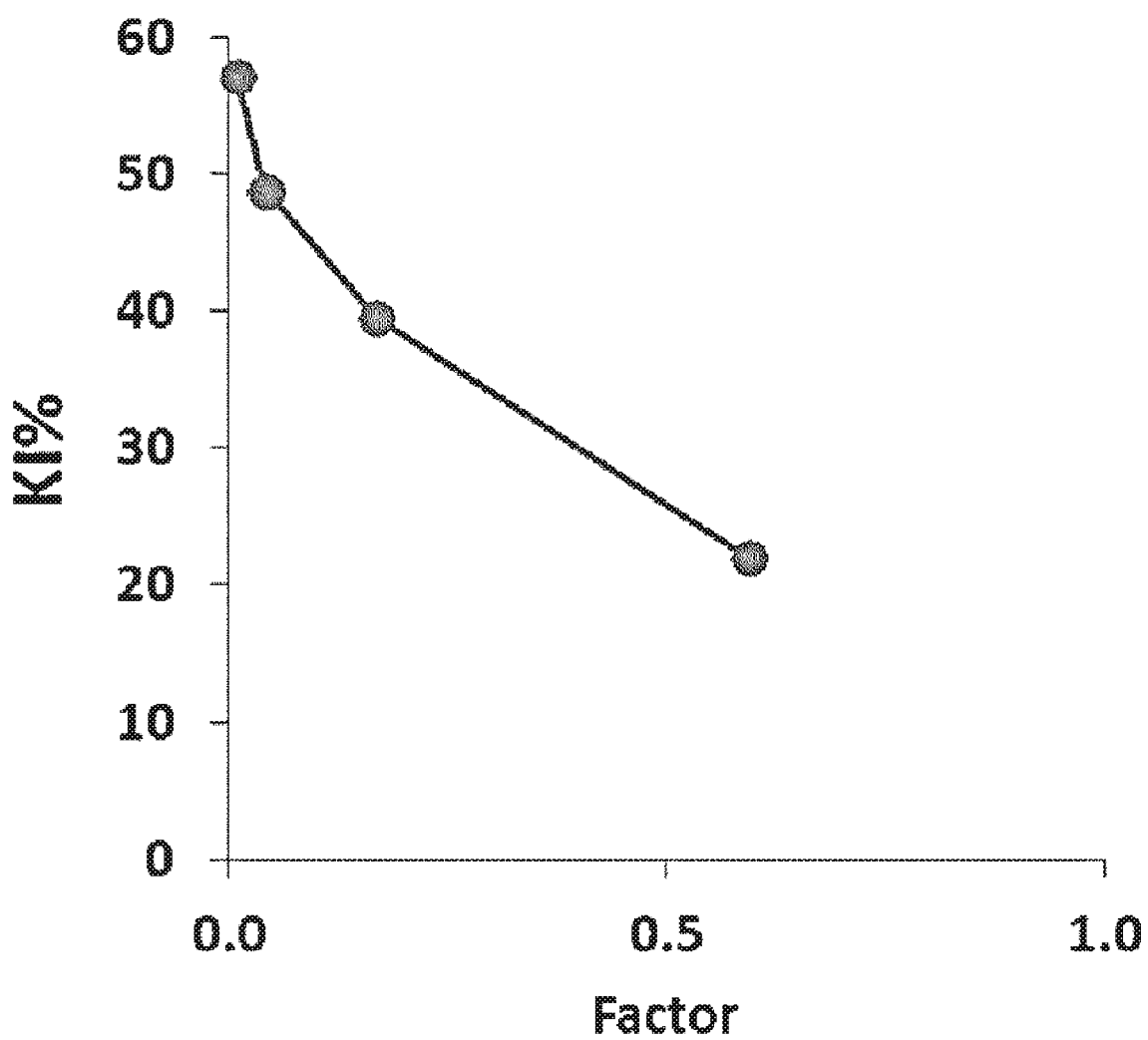
FIG. 15 shows a result obtained by calculating, based on the amount (X) of an amplification product of wild-type IPTKB gene and the amount (Y) of an amplification product of IPTKB gene into which an artificial nucleic acid sequence is inserted, the knock-in efficiency (=100×Y/(X+Y)) and plotting it relative to the Factor value (Example 4). The horizontal axis represents the Factor value and the vertical axis represents the knock-in efficiency (%).
Figure 16:
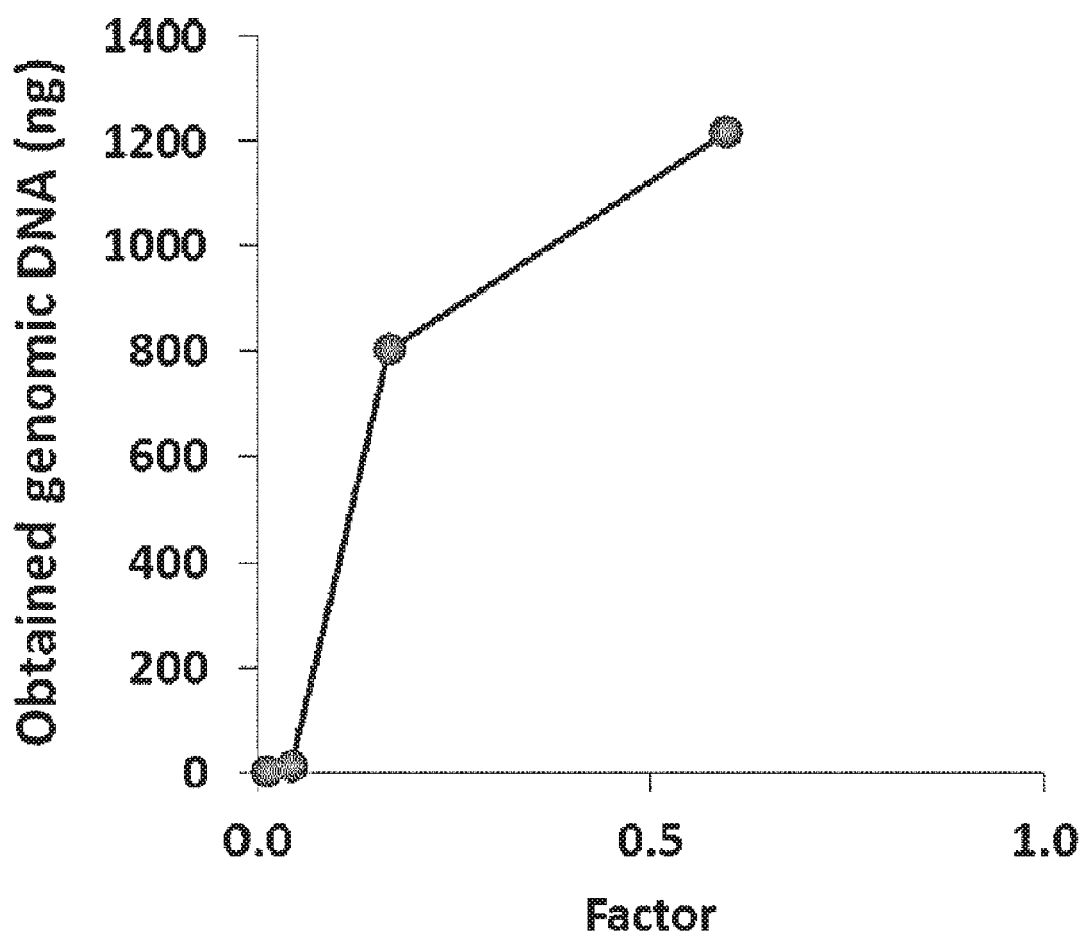
FIG. 16 shows a result obtained by plotting the mass of the genomic DNA collected relative to the Factor value (Example 4). The horizontal axis represents the Factor value and the vertical axis represents the mass of the genomic DNA (ng).

FIG. 15 shows a result of the knock-in efficiency (=100× Y/(X+Y)) calculated by quantifying the amount (X) of the amplification product of wild-type IPTKB gene and the amount (Y) of the amplification product of IPTKB gene into which the artificial nucleic acid sequence is inserted through the quantification of the band concentration. In the figure, the horizontal axis represents the rate of dilution of the selection vector (pEBmultipuro), and the vertical axis represents the knock-in efficiency (%). In addition, the total amount of the genomic DNA collected upon this is shown in FIG. 16. In the figure, the horizontal axis represents the rate of dilution of the selection vector (pEBmultipuro), and the vertical axis represents the amount of the genomic DNA that was not able to be collected. When the Factor value gets lower, the higher knock-in efficiency is obtained. When the Factor value was within a range of 0.011 to 0.043, more efficient modification of the target site in the genome was achieved from the viewpoint of the knock-in efficiency and the amount of the genomic DNA.

Test Example 1: Evaluation of Knock-in Efficiency Via Digital PCR

When a TaqMan probe 1 designed for the outside of homology arms and a probe 2 designed for a gene to be inserted are labeled with different fluorescences and used at the same time, if the number of wells in which both fluorescences are negative is sufficiently large, the genomic DNA molecules are limiting diluted on wells of digital PCR and distributed at 0 to 1 molecule for each well. In wells in which both fluorescences are positive at that condition, both binding sites are thought to be present within the average DNA length that has been divided upon the preparation of the genomic DNA, and that average DNA length is sufficiently short relative to the entire genome of about 3,000,000,000 bps and the possibility that the double-positive is brought about by the DNA nonspecifically inserted into the genome is considerably low; therefore, the double-positive wells are counted as specific gene insertion. The ratio (%) of the number of double-positive wells to the number of the entire probe 2 positive wells is defined as the insertion %.

Example 5: Evaluation of Fragmentation Percentage and Knock-in Efficiency

Following the method described in Example 1, insertion of an artificial nucleic acid sequence (TK gene) was performed to a target site of Adenomatous polyposis *coli* (APC) gene in the genome of a cell. After that, calculation of the fragmentation percentage using parent cells and evaluation of the knock-in efficiency using knock-in cells were performed.

At first, genomic DNA fragments were prepared from the parent cells using a commercially available kit (QIAamp DNA Mini Kit, QIAGEN).

A probe set (Probe A, Probe B) that hybridizes to an endogenous gene (SOD1 gene) with the distance of 1 kb was designed.

A digital PCR method was performed on the genomic DNA fragments as templates using the probe set, and hybridization of the probe pair to the genomic DNA fragments were quantified. Quantitative values are shown in "Table 2." The fragmentation percentage within a region of 1 kb was calculated to be 8.8%.

TABLE 2

| Signal | Quantitative value |
| --- | --- |
| Probe A, Probe B double positive | 1036 |
| Probe A single positive | 107 |
| Probe B single positive | 92 |

Fragmentation percentage (%)=(<sp>)×100/(dp+<sp>)=(107+92)/2×100/(1036+(107+92)/2)=8.8

(wherein, "dp" denotes a hybridization amount of both probes of the probe pair, and <sp> denotes an average value of hybridization amounts of each probe of the probe pair.)

```
Probe A:
                                      (SEQ ID NO: 13)
TCGCCCAATAAAC Digital PCR forward primer of Probe A:
                                      (SEQ ID NO: 14)
AGTCGTTTGGCTTGTGGTGTAA Digital PCR reverse primer of Probe A:
                                      (SEQ ID NO: 15)
GCTAGCAGGATAACAGATGAGTTAAGG Probe B:
                                      (SEQ ID NO: 16)
CTGATGCTTTTTCATTATTAGG Digital PCR forward primer of Probe B:
                                      (SEQ ID NO: 17)
TGGCATCAGCCCTAATCCA Digital PCR reverse primer of Probe B:
                                      (SEQ ID NO: 18)
CATTGCCCAAGTCTCCAACA
```

Probe $P_1$ having a nucleotide sequence complementary to part of the nucleotide sequence of TK gene, and Probe $P_2$ having a nucleotide sequence complementary to the nucleotide sequence outside of the region between homology arms were designed. The distance between a first region to which Probe $P_1$ can hybridize and a second region to which Probe $P_2$ hybridizes was set to be 1 kb.

The chromosome was extracted from knock-in cells under the same conditions as the extraction from the parent cells, and genomic DNA fragments were prepared.

A digital PCR method was performed on the genomic DNA fragments as templates using the probe set, and hybridization of the probe pair to the genomic DNA fragments were quantified. Quantitative values are shown in "Table 3."

TABLE 3

| Signal | Quantitative value |
| --- | --- |
| Probe $P_1$, Probe $P_2$ double positive | 1059 |
| Probe $P_1$ single positive | 213 |
| Probe $P_2$ single positive | 194 |

Insertion percentage of exogenous nucleic acid sequence into locus of interest (%)=DP×100/(DP+SP2)=1059×100/(1059+194)=84.5

Random integration percentage of exogenous nucleic acid sequence into chromosome (%)=SP1×100/(DP+SP1)=194×100/(1059+194)=15.5

```
Probe P₁:
                                      (SEQ ID NO: 19)
ATCGGCTCGGGTACG Digital PCR forward primer of Probe P₁:
                                      (SEQ ID NO: 20)
CCAGCACCCGCCAGTAAGT Digital PCR reverse primer of Probe P₁:
                                      (SEQ ID NO: 21)
TTCGCGCGACGATATCG Probe P₂:
                                      (SEQ ID NO: 22)
GCCACCATGAATGCTTACAATG Digital PCR forward primer of Probe P₂:
                                      (SEQ ID NO: 23)
CACTGTCAAGATAAATCA Digital PCR reverse primer of Probe P₂:
                                      (SEQ ID NO: 24)
TGACTGGAGCAAAGACGGTTT
```

Taking the fragmentation percentage (8.8%) previously calculated into consideration, the insertion percentage after considering the fragmentation was evaluated to be 93.3% (84.5+8.8), and substantially matched with the theoretical value of 100%.

According to this approach, by changing conditions for the knock-in operation, the knock-in efficiency for each condition can be accurately evaluated. Therefore, this approach can be utilized to determine the optimal Factor value in the method of modifying a target site in the genome according to the present invention.

SEQUENCE LISTING FREE TEXT

SEQ ID NO: 1: Nucleotide sequence of exon 3 of APC gene
SEQ ID NO: 2: gRNA recognition sequence in nucleotide sequence of APC gene
SEQ ID NO: 3: Nucleotide sequence of forward primer for APC gene
SEQ ID NO: 4: Nucleotide sequence of reverse primer for APC gene
SEQ ID NO: 5: Nucleotide sequence of amplification product of wild-type APC gene SEQ ID NO: 6: Nucleotide sequence of amplification product of APC gene into which artificial nucleic acid is inserted
SEQ ID NO: 7: gRNA recognition sequence in nucleotide sequence of TNNI1 gene
SEQ ID NO: 8: Nucleotide sequence of forward primer for TNNI1 gene
SEQ ID NO: 9: Nucleotide sequence of forward primer for TNNI1 gene
SEQ ID NO: 10: gRNA recognition sequence of IPTKB gene
SEQ ID NO: 11: Nucleotide sequence of IPTKB gene forward primer
SEQ ID NO: 12: Nucleotide sequence of IPTKB gene reverse primer
SEQ ID NO: 13: Nucleotide sequence of Probe A
SEQ ID NO: 14: Nucleotide sequence of digital PCR forward primer of Probe A
SEQ ID NO: 15: Nucleotide sequence of digital PCR reverse primer of Probe A
SEQ ID NO: 16: Nucleotide sequence of Probe B
SEQ ID NO: 17: Nucleotide sequence of digital PCR forward primer of Probe B
SEQ ID NO: 18: Nucleotide sequence of digital PCR reverse primer of Probe B
SEQ ID NO: 19: Nucleotide sequence of Probe $P_1$
SEQ ID NO: 20: Nucleotide sequence of digital PCR forward primer of Probe $P_1$
SEQ ID NO: 21: Nucleotide sequence of digital PCR reverse primer of Probe $P_1$
SEQ ID NO: 22: Nucleotide sequence of Probe $P_2$
SEQ ID NO: 23: Nucleotide sequence of digital PCR forward primer of Probe $P_2$
SEQ ID NO: 24: Nucleotide sequence of digital PCR reverse primer of Probe $P_2$

The invention claimed is:

1. A method of modifying a target site in the genome of a eukaryotic cell, the method comprising:

(1) introducing into the cell, four separate introduction nucleic acids consisting of:

(a) a template nucleic acid comprising a nucleic acid sequence encoding an RNA-guided nuclease, (b) a template nucleic acid comprising a nucleic acid sequence encoding a guide RNA, or a guide RNA, (c) a template nucleic acid comprising a nucleic acid sequence encoding a selectable marker, wherein the selectable marker is a drug resistance gene, and (d) a targeting template nucleic acid comprising an exogenous nucleic acid sequence; and (2) selecting a cell expressing the selectable marker by culturing the cell after said introducing in a presence of a drug and thereby, obtaining a living cell, wherein the number of moles (C) of (c) the template nucleic acid comprising a nucleic acid sequence encoding a selectable marker is smaller than any of the number of moles (A) of (a) the template nucleic acid comprising a nucleic acid sequence encoding an RNA-guided nuclease, the number of moles (B) of (b) the template nucleic acid comprising a nucleic acid sequence encoding a guide RNA, or the guide RNA, and the number of moles (D) of (d) the targeting template nucleic acid comprising an exogenous nucleic acid sequence, and wherein the ratio of the number obtained by multiplying the number of moles (C) of (c) the template nucleic acid comprising a nucleic acid sequence encoding a selectable marker by the number of types (4) of the introduction nucleic acids to the total of the number of moles (A) of (a) the template nucleic acid comprising a nucleic acid sequence encoding an RNA-guided nuclease, the number of moles (B) of (b) the template nucleic acid comprising a nucleic acid sequence encoding a guide RNA, or the guide RNA, the number of moles (C) of (c) the template nucleic acid comprising a nucleic acid sequence encoding a selectable marker, and the number of moles (D) of (d) the template nucleic acid comprising an exogenous nucleic acid sequence (C×4/(A+B+C+D)) is 0.01 to 0.04.

2. The method according to claim 1, wherein any one of the introduction nucleic acids is a plasmid vector.

3. The method according to claim 1, wherein the RNA-guided nuclease is a Cas9 nuclease or a Cas9 nickase.

4. The method according to claim 1, wherein the RNA-guided nuclease is a Cpf1 nuclease.

* * * * *

```
                        SEQUENCE LISTING

<160> NUMBER OF SEQ ID NOS: 28

<210> SEQ ID NO 1
<211> LENGTH: 202
<212> TYPE: DNA
<213> ORGANISM: Homo sapiens

<400> SEQUENCE: 1
agcttaactt agatagcagt aatttccctg gagtaaaact gcggtcaaaa atgtccctcc        60
gttcttatgg aagccgggaa ggatctgtat caagccgttc tggagagtgc agtcctgttc       120
ctatgggttc atttccaaga agagggtttg taaatggaag cagagaaagt actggatatt       180
tagaagaact tgagaaagag ag                                                202

<210> SEQ ID NO 2
<211> LENGTH: 24
<212> TYPE: DNA
<213> ORGANISM: Homo sapiens

<400> SEQUENCE: 2
ccctccgttc ttatggaagc cggg                                               24

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Forward primer for APC gene

<400> SEQUENCE: 3
cttgcacaga gactccccat aatcacc                                            27

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Reverse primer for APC gene

<400> SEQUENCE: 4
```

```
actttctctg cttccattta caaaccctct tc                                   32
```

<210> SEQ ID NO 5
<211> LENGTH: 1256
<212> TYPE: DNA
<213> ORGANISM: Homo sapiens

<400> SEQUENCE: 5

```
cttgcacaga gactccccat aatcaccatt atctcaaaat atcactatta ttatttggcc     60
atgatttatt tattaataat gaataatagg taatatatat aaggtgcgtg ctttgagagt    120
gatctgaatt tttttctcag catacttaaa tgtcaagaaa tacagaatca tgtcttgaag    180
ttatttagaa tttcatgtta atatattgtg ttcttttaa caggaagtac ttaaacaact     240
acaaggaagt attgaagatg aagctatggc ttcttctgga cagattgatt tattagagcg    300
tcttaaaggt agattttaaa aaggtgtttt aaaataattt tttaagctca aattgtcatc    360
tttaggtgtg tagatccaag tacagcttct ctcgatttgg gtgttggtat cagttttctt    420
ggtatgttag ccttaccctc aggatgtaat tgttaaagta caaataaata aaaaatgtat    480
ttgtgtgtca tttcttcagt taaacattta actggctttg aatgaactat tttaaatccc    540
tcccttaaat aattttcggc tctttgtaaa gcttgttgct attctgccag tcactaaata    600
gggctttagt attctatatg ccatagactt gagcctactg tttcattgga agaagtattg    660
tcttcttcat tcaggataga aatactttaa ccttttcaca tatataagtt gattataatt    720
cattttagc agttttaaaa ggatatcttt ctcattctgt tgcttgaaaa ttccagtgtc     780
agaacagaga aagtgcttga taataattga agccagacag agaaattact tttggattct    840
aaaatattat ttagaggaag tctaaggaag tacattttat ctaattttcc tttaacacac    900
tccttatttt taccctgacc caagtggact tttcagggaa agtcctaaat aattttgtt     960
ttcagtcatg tatatttgtg gttaaaatgt aaacctaata tttcacttta aaataatata   1020
acattaagaa tattttagac tgcttaaagc aattgttgta taaaaacttg tttctatttt   1080
atttagagct taacttagat agcagtaatt tccctggagt aaaactgcgg tcaaaaatgt   1140
ccctccgttc ttatggaagc cgggaaggat ctgtatcaag ccgttctgga gagtgcagtc   1200
ctgttcctat gggttcattt ccaagaagag ggtttgtaaa tggaagcaga gaaagt      1256
```

<210> SEQ ID NO 6
<211> LENGTH: 1191
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Amplification product of APC gene having an artificial nucleic acid inserted

<400> SEQUENCE: 6

```
cttgcacaga gactccccat aatcaccatt atctcaaaat atcactatta ttatttggcc     60
atgatttatt tattaataat gaataatagg taatatatat aaggtgcgtg ctttgagagt    120
gatctgaatt tttttctcag catacttaaa tgtcaagaaa tacagaatca tgtcttgaag    180
ttatttagaa tttcatgtta atatattgtg ttcttttaa caggaagtac ttaaacaact     240
acaaggaagt attgaagatg aagctatggc ttcttctgga cagattgatt tattagagcg    300
tcttaaaggt agattttaaa aaggtgtttt aaaataattt tttaagctca aattgtcatc    360
tttaggtgtg tagatccaag tacagcttct ctcgatttgg gtgttggtat cagttttctt    420
```

-continued

```
ggtatgttag ccttaccctc aggatgtaat tgttaaagta caaataaata aaaaatgtat    480
ttgtgtgtca tttcttcagt taaacattta actggctttg aatgaactat tttaaatccc    540
tcccttaaat aattttcggc tctttgtaaa gcttgttgct attctgccag tcactaaata    600
gggctttagt attctatatg ccatagactt gagcctactg tttcattgga agaagtattg    660
tcttcttcat tcaggataga aatactttaa ccttttcaca tatataagtt gattataatt    720 cattttttagc agttttaaaa ggatatcttt ctcattctgt tgcttgaaaa ttccagtgtc    780
agaacagaga aagtgcttga taataattga agccagacag agaaattact tttggattct    840
aaaatattat ttagaggaag tctaaggaag tacattttat ctaattttcc tttaacacac    900
tccttatttt taccctgacc caagtggact tttcagggaa agtcctaaat aattttttgtt   960 ttcagtcatg tatatttgtg gttaaaatgt aaacctaata tttcacttta aaataatata    1020
acattaagaa tattttagac tgcttaaagc aattgttgta taaaaacttg tttctatttt    1080
atttagagct taacttagat agcagtaatt tccctggagt aaaactgcgg tcaaaaatgt    1140
cccatgggtt catttccaag aagagggttt gtaaatggaa gcagagaaag t             1191
```

<210> SEQ ID NO 7
<211> LENGTH: 24
<212> TYPE: DNA
<213> ORGANISM: Homo sapiens

<400> SEQUENCE: 7

```
gagtctccga cctcacaata gagg                                            24
```

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: forward primer for TNNI1 gene

<400> SEQUENCE: 8

```
gaacgtggag gccatgtct                                                  19
```

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Reverse primer for TNNI1 gene

<400> SEQUENCE: 9

```
taagtacaac ccgcctgcc                                                  19
```

<210> SEQ ID NO 10
<211> LENGTH: 27
<212> TYPE: DNA
<213> ORGANISM: Homo sapiens

<400> SEQUENCE: 10

```
ttttcccaaa gtcgatcatc cacactt                                         27
```

<210> SEQ ID NO 11

```
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Forward primer for IPTKB gene

<400> SEQUENCE: 11
attgagcccc gagaggtagc catcct                                    26

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Reverse primer for IPTKB gene

<400> SEQUENCE: 12
gggcttcagc tcacccttca c                                         21

<210> SEQ ID NO 13
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Probe A

<400> SEQUENCE: 13
tcgcccaata aac                                                  13

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Probe A forward primer for digital PCR

<400> SEQUENCE: 14
agtcgtttgg cttgtggtgt aa                                        22

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Probe A reverse primer for digital PCR

<400> SEQUENCE: 15
gctagcagga taacagatga gttaagg                                   27

<210> SEQ ID NO 16
<211> LENGTH: 22
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Probe B

<400> SEQUENCE: 16
ctgatgcttt ttcattatta gg                                            22

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Probe B foward primer for digital PCR

<400> SEQUENCE: 17
tggcatcagc cctaatcca                                                19

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Probe B reverse primer for digital PCR

<400> SEQUENCE: 18
cattgcccaa gtctccaaca                                               20

<210> SEQ ID NO 19
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Probe P1

<400> SEQUENCE: 19
atcggctcgg gtacg                                                    15

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Probe P1 foward primer for digital PCR

<400> SEQUENCE: 20
ccagcacccg ccagtaagt                                                19

<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Probe P1 reverse primer for digital PCR
```

<400> SEQUENCE: 21
ttcgcgcgac gatatcg                                                        17

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Probe P2

<400> SEQUENCE: 22
gccaccatga atgcttacaa tg                                                  22

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Probe P2 foward primer for digital PCR

<400> SEQUENCE: 23
cactgtcaag ataaatca                                                       18

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Probe P2 reverse primer for digital PCR

<400> SEQUENCE: 24
tgactggagc aaagacggtt t                                                   21

<210> SEQ ID NO 25
<211> LENGTH: 420
<212> TYPE: DNA
<213> ORGANISM: Homo sapiens

<400> SEQUENCE: 25
tctgctgcct gtctgaaaat ggggattgga attgcaggca cccaactgtc cggcctgagc         60
gagcctcccc acctggtcac ccaggccccg ggccgcagtg ggagggcga ggccgggct          120 tcagctcacc cttcaccccc atgttctcct caggtcattg gcagctccct cctcttcatc        180
cacgacaaga aggaacaggc caaagtgtgg atgatcgact ttgggaaaac cacgcccctg        240
cctgagggcc agaccctgca gcatgacgtc cctggcagg aggggaaccg ggaggatggc         300
tacctctcgg ggctcaataa cctcgtcgac atcctgaccg agatgtccca ggatgcccca        360
ctcgcctgag ctgccacgc cctcctggc cccgcctgg gcctcctttc ctcctcctgt          420

<210> SEQ ID NO 26
<211> LENGTH: 122
<212> TYPE: PRT
<213> ORGANISM: Homo sapiens

<400> SEQUENCE: 26

```
Ser Ala Ala Cys Leu Lys Met Gly Ile Gly Ile Ala Gly Thr Gln Leu
1               5                   10                  15

Ser Gly Leu Ser Glu Pro Pro His Leu Val Thr Gln Ala Pro Gly Arg
            20                  25                  30

Ser Gly Glu Gly Glu Ala Arg Ala Ser Ala His Pro Ser Pro Pro Cys
            35                  40                  45

Ser Pro Gln Val Ile Gly Ser Ser Leu Leu Phe Ile His Asp Lys Lys
        50                  55                  60

Glu Gln Ala Lys Val Trp Met Ile Asp Phe Gly Lys Thr Thr Pro Leu
65                  70                  75                  80

Pro Glu Gly Gln Thr Leu Gln His Asp Val Pro Trp Gln Glu Gly Asn
                85                  90                  95

Arg Glu Asp Gly Tyr Leu Ser Gly Leu Asn Asn Leu Val Asp Ile Leu
            100                 105                 110

Thr Glu Met Ser Gln Asp Ala Pro Leu Ala
            115                 120

<210> SEQ ID NO 27
<211> LENGTH: 240
<212> TYPE: DNA
<213> ORGANISM: Homo sapiens

<400> SEQUENCE: 27
tctattttat ttagagctta acttagatag cagtaatttc cctggagtaa aactgcggtc      60
aaaaatgtcc ctccgttctt atggaagccg ggaaggatct gtatcaagcc gttctggaga     120
gtgcagtcct gttcctatgg gttcatttcc aagaagaggg tttgtaaatg gaagcagaga     180
aagtactgga tatttagaag aacttgagaa agagaggtaa cttttcttca tatagtaaac     240

<210> SEQ ID NO 28
<211> LENGTH: 67
<212> TYPE: PRT
<213> ORGANISM: Homo sapiens

<400> SEQUENCE: 28

Leu Asn Leu Asp Ser Ser Asn Phe Pro Gly Val Lys Leu Arg Ser Lys
1               5                   10                  15

Met Ser Leu Arg Ser Tyr Gly Ser Arg Glu Gly Ser Val Ser Ser Arg
            20                  25                  30

Ser Gly Glu Cys Ser Pro Val Pro Met Gly Ser Phe Pro Arg Arg Gly
        35                  40                  45

Phe Val Asn Gly Ser Arg Glu Ser Thr Gly Tyr Leu Glu Glu Leu Glu
    50                  55                  60

Lys Glu Arg
65
```